United States Patent
Chin et al.

(10) Patent No.: US 11,406,375 B2
(45) Date of Patent: Aug. 9, 2022

(54) PURSESTRING SUTURE RETRACTOR AND METHOD OF USE

(71) Applicant: MITRx, Inc., San Jose, CA (US)

(72) Inventors: Albert K. Chin, Palo Alto, CA (US);
Murali Dharan, Danville, CA (US);
John Ashley, Danville, CA (US)

(73) Assignee: MITRx, Inc., San Jose, CA (US)

( * ) Notice: Subject to any disclaimer, the term of this patent is extended or adjusted under 35 U.S.C. 154(b) by 65 days.

(21) Appl. No.: 16/918,027

(22) Filed: Jul. 1, 2020

(65) Prior Publication Data

US 2021/0085310 A1 Mar. 25, 2021

Related U.S. Application Data

(63) Continuation of application No. PCT/US2019/012538, filed on Jan. 7, 2019.
(Continued)

(51) Int. Cl.
*A61B 17/04* (2006.01)
*A61B 17/02* (2006.01)
*A61B 17/34* (2006.01)

(52) U.S. Cl.
CPC ...... *A61B 17/0469* (2013.01); *A61B 17/0206* (2013.01); *A61B 17/0218* (2013.01);
(Continued)

(58) Field of Classification Search
CPC ........ A61B 17/0469; A61B 2017/1142; A61B 2017/047; A61B 17/02; A61B 2017/0237;
(Continued)

(56) References Cited

U.S. PATENT DOCUMENTS

| 4,813,407 A | 3/1989 | Vogen |
| 5,293,863 A | 3/1994 | Zhu et al. |

(Continued)

FOREIGN PATENT DOCUMENTS

| WO | WO-9730659 A1 | 8/1997 |
| WO | WO-0018303 A1 | 4/2000 |

(Continued)

OTHER PUBLICATIONS

Ad, et al., Minimally invasive mitral valve surgery without aortic cross-clamping and with femoral cannulation is not associated with increased risk of stroke compared with traditional mitral valve surgery: a propensity socre-matched analysis. Eur J Cardiothorac Surg (2015); 48:868-872.
(Continued)

*Primary Examiner* — Tan-Uyen T Ho
*Assistant Examiner* — Bridget E. Rabaglia
(74) *Attorney, Agent, or Firm* — Wilson Sonsini Goodrich & Rosati

(57) ABSTRACT

Systems, devices, and methods for endoscopically retracting a target tissue. The device includes a first shaft and a second shaft slidably coupled thereto. An internal member extends in a transverse direction from the first shaft and is configured for advancement through a penetration in the target tissue to atraumatically engage a distal surface of the target tissue after being advanced therethrough. A pair of external members extend from the second shaft generally parallel to the transverse direction. The external members are spaced apart and are configured to atraumatically engage a proximal surface of the target tissue when the internal member is moved longitudinally relative to the external members. The internal member applies traction to the target tissue when retracted past the pair of external members, which apply counter-traction to the target tissue on opposing lateral sides (Continued)

of the internal member, to re-shape the target tissue and enable subsequent suture placement.

22 Claims, 25 Drawing Sheets

Related U.S. Application Data

(60) Provisional application No. 62/614,326, filed on Jan. 5, 2018.

(52) U.S. Cl.
CPC .. *A61B 17/3417* (2013.01); *A61B 2017/0237* (2013.01); *A61B 2017/047* (2013.01); *A61B 2017/0474* (2013.01); *A61B 2017/3419* (2013.01); *A61B 2217/005* (2013.01)

(58) Field of Classification Search
CPC ............ A61B 17/0206; A61B 17/0218; A61B 17/0281; A61B 17/04; A61B 17/3417; A61B 2017/3419; A61B 2217/005
See application file for complete search history.

(56) References Cited

U.S. PATENT DOCUMENTS

| | | | |
|---|---|---|---|
| 5,571,215 | A | 11/1996 | Sterman et al. |
| 5,913,876 | A | 6/1999 | Taylor et al. |
| 6,074,343 | A | 6/2000 | Nathanson et al. |
| 6,346,077 | B1 | 2/2002 | Taylor et al. |
| 6,402,780 | B2 | 6/2002 | Williamson, IV et al. |
| 7,618,367 | B2 | 11/2009 | Martin et al. |
| D675,319 | S | 1/2013 | Huertgen et al. |
| 8,394,015 | B2 | 3/2013 | Dibiasio et al. |
| 8,398,658 | B2 * | 3/2013 | Roshanali .......... A61B 17/0057 606/139 |
| 8,500,757 | B2 | 8/2013 | Miraki et al. |
| 8,696,689 | B2 | 4/2014 | Tuval et al. |
| 8,870,900 | B2 | 10/2014 | Julian et al. |
| 8,882,660 | B2 | 11/2014 | Phee et al. |
| 8,926,640 | B2 | 1/2015 | Sauer et al. |
| 8,926,657 | B2 | 1/2015 | Litvack et al. |
| 8,939,936 | B2 | 1/2015 | Shanley |
| 8,939,937 | B2 | 1/2015 | Shanley |
| 9,050,129 | B2 | 6/2015 | Rothstein et al. |
| 9,226,824 | B2 | 1/2016 | Miraki |
| 9,254,141 | B2 | 2/2016 | Morris et al. |
| 9,265,497 | B2 | 2/2016 | Teichman et al. |
| 9,277,915 | B2 | 3/2016 | Belson et al. |
| 9,282,954 | B2 | 3/2016 | Bolotin |
| 9,301,842 | B2 | 4/2016 | Bielefeld |
| 9,398,910 | B2 | 7/2016 | Shanley et al. |
| 9,532,773 | B2 | 1/2017 | Jimenez et al. |
| 9,579,097 | B2 | 2/2017 | Shluzas |
| 9,610,097 | B2 | 4/2017 | Milo |
| 9,675,338 | B2 | 6/2017 | Shanley et al. |
| 9,681,861 | B2 | 6/2017 | Heisel et al. |
| 9,707,076 | B2 | 7/2017 | Stack et al. |
| 9,717,594 | B2 | 8/2017 | Jimenez et al. |
| 9,724,079 | B2 | 8/2017 | Shanley |
| 9,730,687 | B2 | 8/2017 | Shluzas et al. |
| 9,730,690 | B2 | 8/2017 | Shanley et al. |
| 9,782,168 | B2 | 10/2017 | Shanley et al. |
| 10,433,960 | B1 | 10/2019 | Sutherland et al. |
| 2005/0065397 | A1 | 3/2005 | Saadat et al. |
| 2005/0101984 | A1 | 5/2005 | Chanduszko et al. |
| 2006/0020271 | A1 | 1/2006 | Stewart et al. |
| 2007/0255314 | A1 | 11/2007 | Forsberg |
| 2008/0021552 | A1 | 1/2008 | Gabbay |
| 2009/0093809 | A1 | 4/2009 | Anderson et al. |
| 2009/0259097 | A1 | 10/2009 | Thompson |
| 2009/0275893 | A1 | 11/2009 | Dibiasio et al. |
| 2010/0041942 | A1 | 2/2010 | Okada |
| 2010/0160725 | A1 | 6/2010 | Kiser et al. |
| 2011/0144450 | A1 | 6/2011 | Paolitto et al. |
| 2011/0208297 | A1 | 8/2011 | Tuval et al. |
| 2012/0065662 | A1 | 3/2012 | Van Der Burg et al. |
| 2012/0123531 | A1 | 5/2012 | Tsukashima et al. |
| 2013/0190726 | A1 | 7/2013 | Kesner et al. |
| 2013/0267785 | A1 | 10/2013 | Sutherland et al. |
| 2013/0267786 | A1 | 10/2013 | Vayser et al. |
| 2014/0114306 | A1 | 4/2014 | Harada et al. |
| 2014/0222031 | A1 | 8/2014 | Stack et al. |
| 2014/0222136 | A1 | 8/2014 | Geist et al. |
| 2014/0371789 | A1 | 12/2014 | Hariton et al. |
| 2015/0012085 | A1 | 1/2015 | Salahieh et al. |
| 2015/0045624 | A1 | 2/2015 | Stack |
| 2015/0328001 | A1 | 11/2015 | McLean et al. |
| 2017/0231477 | A1 | 8/2017 | Del Nido et al. |
| 2019/0365535 | A1 | 12/2019 | Sutherland et al. |
| 2020/0222078 | A1 | 7/2020 | Dharan et al. |

FOREIGN PATENT DOCUMENTS

| | | |
|---|---|---|
| WO | WO-03013367 A2 | 2/2003 |
| WO | WO-2006020920 A2 | 2/2006 |
| WO | WO-2008134267 A2 | 11/2008 |
| WO | WO-2009134701 A2 | 11/2009 |
| WO | WO-2013023016 A1 | 2/2013 |
| WO | WO-2013137094 A1 | 9/2013 |
| WO | WO-2015119780 A1 | 8/2015 |
| WO | WO-2019014643 A1 | 1/2019 |
| WO | WO-2019136378 A1 | 7/2019 |
| WO | WO-2020146889 A1 | 7/2020 |

OTHER PUBLICATIONS

Alturi, et al., Minimally invasive mitral valve surgery is associated with equivalent cost and shorter hospital stay when compared to traditional sternotomy. Journal of Thoracic and Cardiovascular Surgery (2016); 151(2):385-388.

Ataollahi, et al., Cardioscopic tool-delivery instrument for beating-heart surgery. IEEE ASME Trans Mechatron, 21(1): 584-590 (2017).

Bentala, et al., Comparing the endo-aortic balloon and the external aortic clamp in minimally invasive mitral valve surgery. Interact CardioVasc Thorac Surg (2015); 21:359-365.

Bouhout, et al., Review: Minimally invasive heart valve surgery. Canadian Journal of Cardiology (2017); 33:1129-1137.

Boulemden, et al., Atrial approaches to the mitral valve: is there a difference in postoperative rhythm disturbance and permanent pacemaker implantation? Interactive Cardiovascular and Thoracic Surgery (2018); 1-7.

Casselman, et al., Endoaortic clamping does not increase the risk of stroke in minimal access mitral valve surgery: a multicenter experience. Ann Thorac Surg (2015); 100:1334-1339.

Cuartas, et al., Mitral valve repair: robotic and other minimally invasive approaches. Progress in Cardiovascular Diseases (2017); 60:394-404.

Dapunt, et al., First-in-man transcervical savr using a novel access system. ISMICS: Abstract (2016); Accessed on Jul. 8, 2017; http://meetings.ismics.org/abstracts/2015/C19.cgi.

Dapunt et al., First-in-man transcervical surgical aortic valve replacement using the corevista system. Innovations 2016 11(2): 84-93.

Dapunt, et al., New Less Invasive Approach for Direct Aortic Transcatheter Aortic Valve Replacement Using Novel CoreVista Tanscervical Access System. Cardiovascular Interventions, vol. 9, No. 7, 2016.

De Praetere, et al., Starting minimally invasive valve surgery using endoclamp technology safety and results of a starting surgeon. Interactive CardioVascular and Thoracic Surgery (2015); 20:351-358.

Del Giglio, et al., Right anterior mini-thoracotomy vs. conventional sternotomy for aortic valve replacement: a propensity-matched comparison. J Thorac Dis (2018); 10(3):1588-1595.

Dieberg, et al., Minimally invasive cardiac surgery: a systematic review and meta-analysis. International Journal of Cardiology (2016); 223:554-560.

(56) References Cited

OTHER PUBLICATIONS

Esposito, et al., Left atrial roof an alternative minimal approach for mitral valve surgery. Innovations (2012); 7(6):417-420.
Goldstone, et al., Is minimally invasive thorascopic surgery the new benchmark for treating mitral valve disease? Ann Cardiothorac Surg 2016; 5(6): 567-572.
Grossi, et al., Evolution of operative techniques and perfusion strategies for minimally invasive mitral valve repair. Journal of Thoracic and Cardiovascular Surgery (2012); 143(4S):S68-S70.
Hawkins, et al., Minimally invasive mitral valve surgery is associated with excellent resource utilization, cost, and outcomes. Journal of Thoracic and Cardiovascular Surgery (2018); 1-10.
Iribarne, et al., The golden age of minimally invasive cardiotoracic surgery: current and future perspectives. Future Cardiol (2011); 7(3):333-346.
Javadikasgari, et al., Minimally invasive mitral valve repair. Heart (2018); 104: 861-867.
Kawata, et al., Beating-heart mitral valve suture annuloplasty under real-time three-dimensional echocardiography guidance: an ex vivo study. Interactive Cardiovascular and Thoracic Surgery 11 (2010) 6-9.
Kiser, Andy, M.D., Is Supra-Sternal Direct Aortic Access an Alternative to Trans-Thoracic Access for TAVR? An introduction to the Aegis Surgical System, Transcatheter Valve Therapies 2017.
Kiser, et al., Suprasternal direct aortic approach transcatheter aortic valve replacement avoids sternotomy and thoracotomy: first-in-man experience. European Journal of Cardio-Thoracic Surgery (2015); 48:778-784.
Koprivanac, et al., Degenerative mitral valve disease-contemporary surgical approaches and repair techniques. Ann Cardiothorac Surg (2017); 6(1):38-46.
Lamelas, et al., Isolated and concomitant minimally invasive minithoracotomy aortic valve surgery. Journal of Thoracic and Cardiovascular Surgery (2018); 155(3).
Lange, et al., Right minithoracotomy versus full sternotomy for mitral valve repair: a propensity matched comparison. Ann Thorac Surg (2017); 103:573-579.
Little, et al. Revisiting the dome approach for partial sternotomy/minimally invasive mitral valve surgery. Ann Thorac Surg (2009); 87:694-697.
Massimiano, et al., Minimally invasive fibrillating heart surgery: a safe and effective approach for mitral valve and surgical ablation for atrial fibrillation. Ann Thorac Surg (2013); 96:520-527.
Miceli, et al., Minimally invasive mitral valve repair through right minithoracotomy in the setting of degenerative mitral regurgitation: early outcomes and long-term follow-up; Ann Cardiothoracic Surg 2015; 4(5): 422-427.
Okamoto, et al., Designing innovative retractors and devices to facilitate mitral valve repair surgery. Ann Cardiothorac Surg (2015); 4(4): 364-369.
PCT/US18/42171 Search Report & Written Opinion dated Sep. 13, 2018.
PCT/US19/12538 Search Report & Written Opinion dated May 6, 2019.
Poffo, et al., Periareolar access for minimally invasive cardiac surgery. Innovations (2018); 13(1): 65-69.
Qiu, et al., Does full sternotomy have more significant impact than the cadiopulmonary bypass time in patients of mitral valve surgery? Journal of Cardiothoracic Surgery (2018); 13:29.
Sakaguchi, et al., Minimally invasive mitral valve repair through right minitoracotomy. Circ J (2018); 82: 1705-1711.
Salerno, et al., Efficacy, feasibility, and pitfalls of transseptal approach in beating-heart mitral valve surgery. J Card Surg (2009); 24:495-498.
Santana, et al., Is a minimally invasive approach for mitral valve surgery more cost-effective than median sternotomy? Interact CardioVasc Thorac Surg (2016); 22:97-100.
Seitz, et al., Minimally invasive aortic valve replacement via right anterior mini-thoracotomy: propensity matched initial experience. Heart, Lung and Circulation (2017), https://doi.org/10.1016/j.hlc.2017.11.012.
Spadaccio, et al., Transcervical transcathether mitral valve replacement (TMVR): a proof of principle; ISMICS: Abstract (2016); Accessed on Jul. 6, 2017, Available at http:meetings.ismics.org/abstracts/2016/CMP32.cgi.
Speziale, et al., A simplified technique for complex mitral valve regurgitation via minimally invasive approach, Ann Thoracic Surg (2018), doi: 10.1016/j.athoracsur.2018.01.010.
Sundermann, et al., Mitral valve reconstruction—surgical techniques and results. Swiss Med Mkly (2012); 142:w13715.
Taguchi, et al., Minimally invasive mitral valve repair via right mini-thoracotomy in patient with myelodysplastic syndrome. Journal of Cardiothoracic Surgery (2018); 13:45.
U.S. Appl. No. 12/642,137 File History.
U.S. Appl. No. 13/975,258 File History.
U.S. Appl. No. 14/453,463 File History.
Vallabhajosyula, et al., Minimally invasive port access approach for reoperations on the mitral valve. Ann Thorac Surg (2015); 100:68-73.
Van Preet, Minimally invasive surgical mitral valve repair: state of the art review. Interventional Cardiology Review (2018); 13(1):14-19.
Vasilyev, et al., A novel cardioport for beating-heart image-guided intracardiac surgery. J Thorac Cardiovasc Surg. 2011 142(6): 1545-1551.
Yozu, et al., New innovative instruments facilitate both direct-vision and endoscopic-assisted mini-mitral valve surgery. Journal of Thoracic and Cardiovascular Surgery (2012); 143(4S): S82-S85.
EP19736043.1 Extended Search Report dated Extended Search Report dated Jan. 25, 2022.
EP188832840.5 EP Search Report dated Feb. 24, 2021.
Co-pending U.S. Appl. No. 17/364,692, inventors Dharan; Murali et al., filed on Sep. 30, 2021.
PCT/US20/13369 Search Report & Written Opinion dated Apr. 13, 2020.
Saksena et al. The superior approach to the mitral valve: a review of clinical experience. Annals of Thoracic Surgery, vol. 12, issue 2, 1971, pp. 145-153.

* cited by examiner

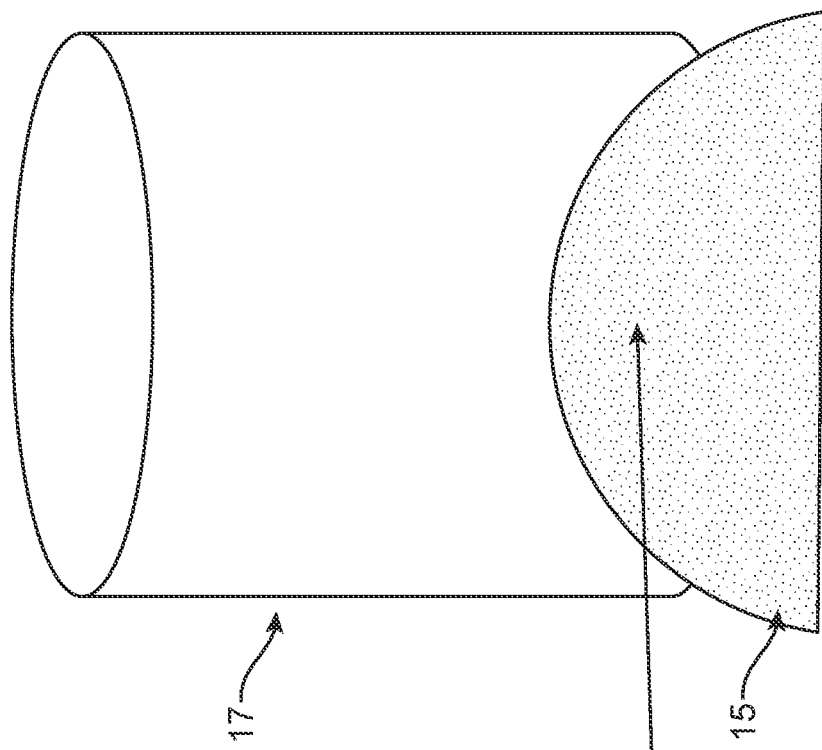
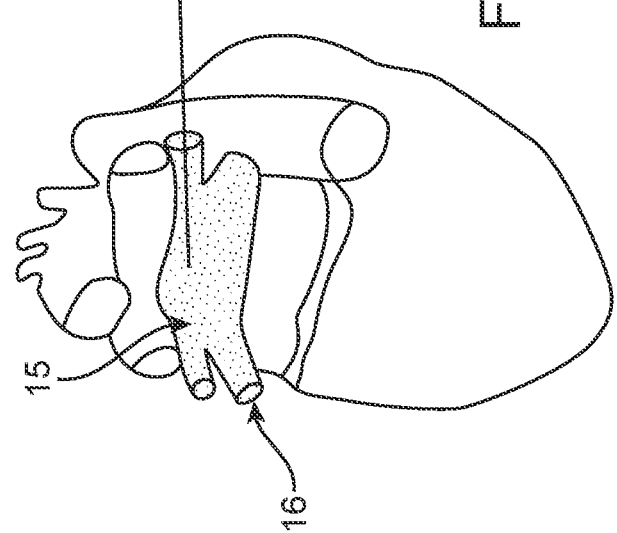
FIG. 2A
FIG. 2B

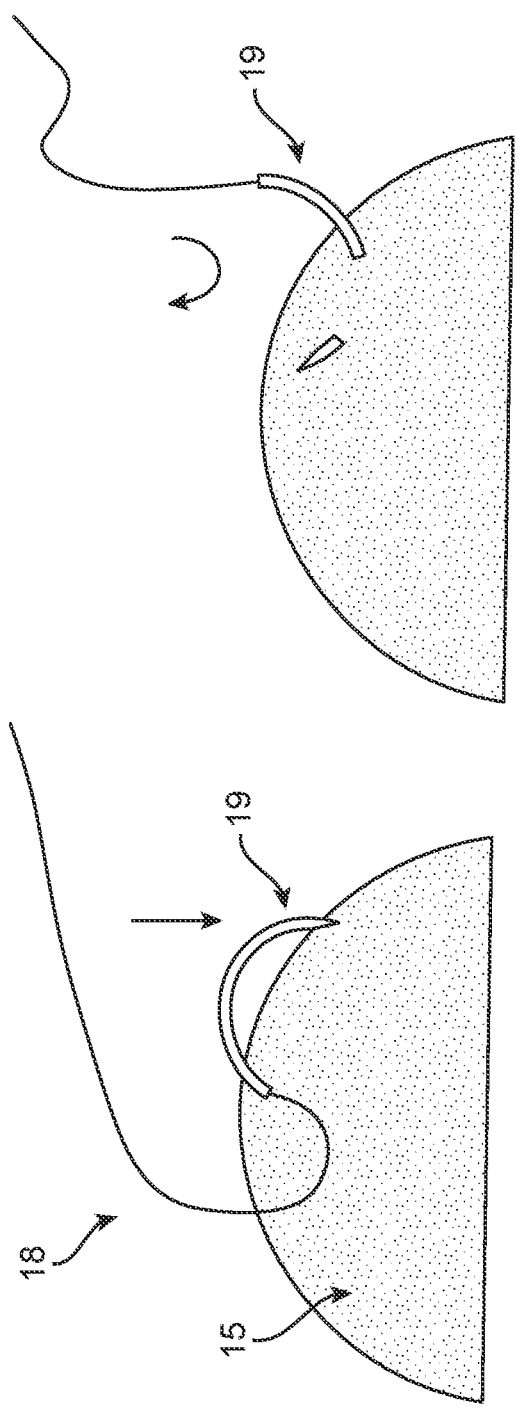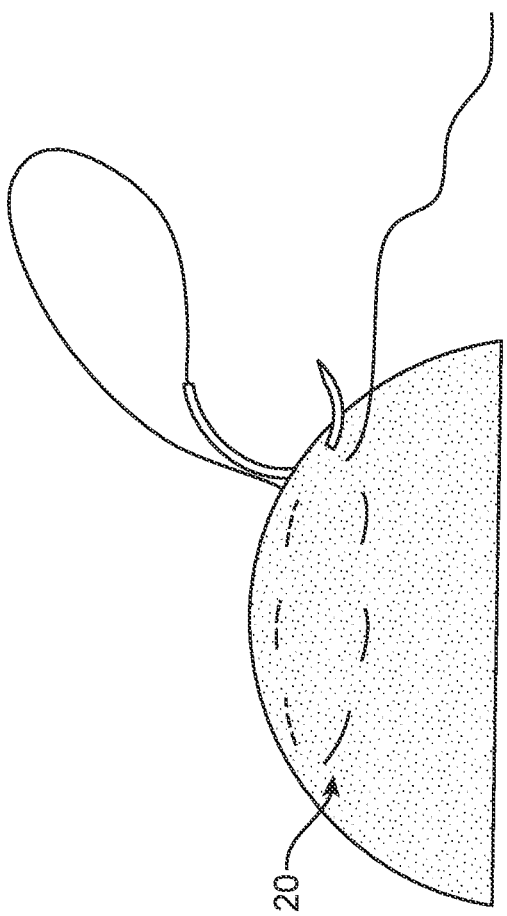
FIG. 3A (PRIOR ART)
FIG. 3B (PRIOR ART)
FIG. 3C (PRIOR ART)

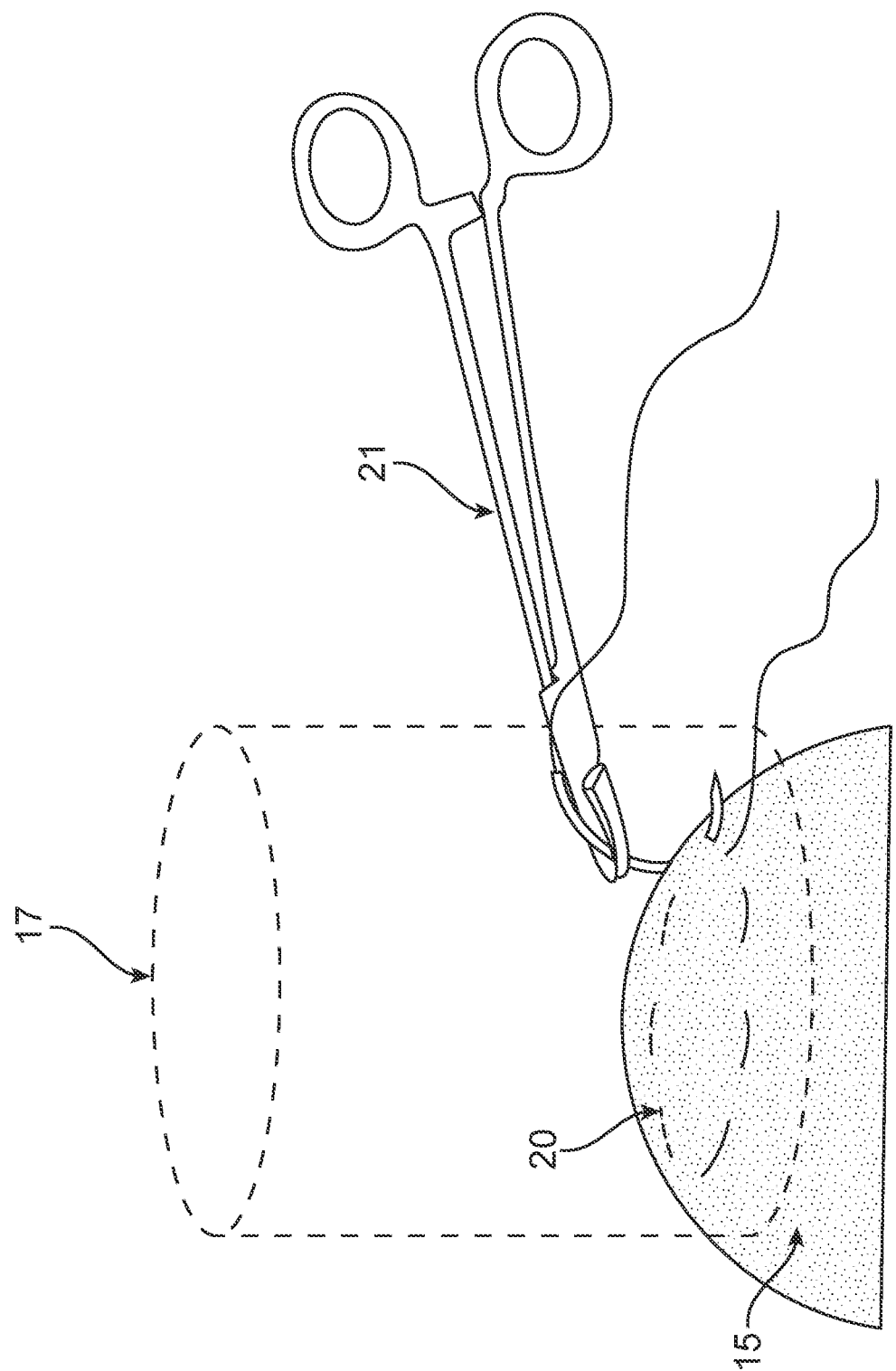

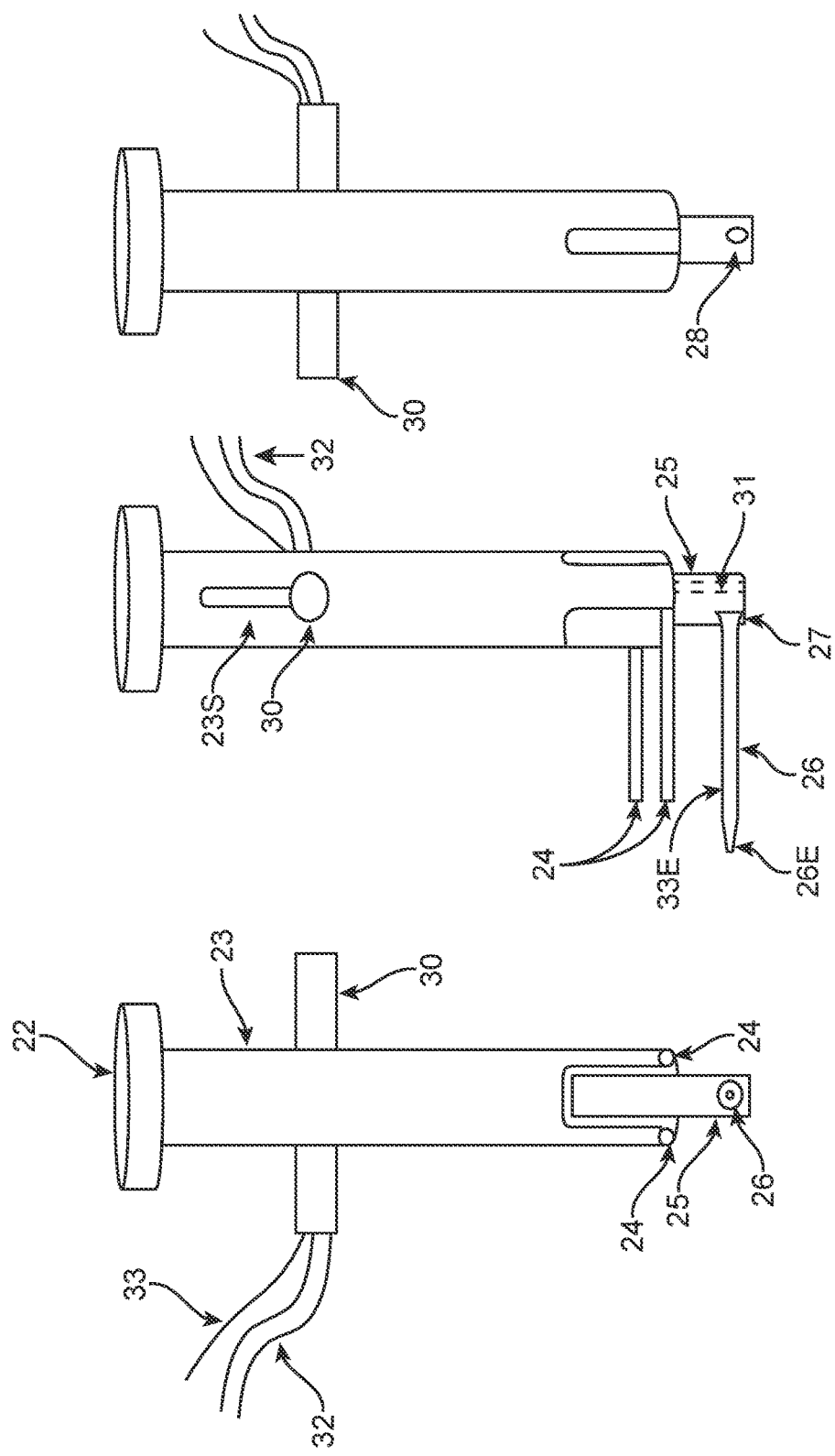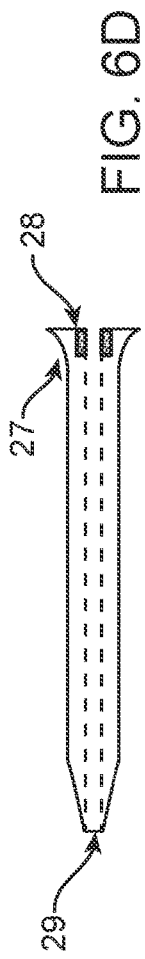
FIG. 6A  FIG. 6B  FIG. 6C  FIG. 6D

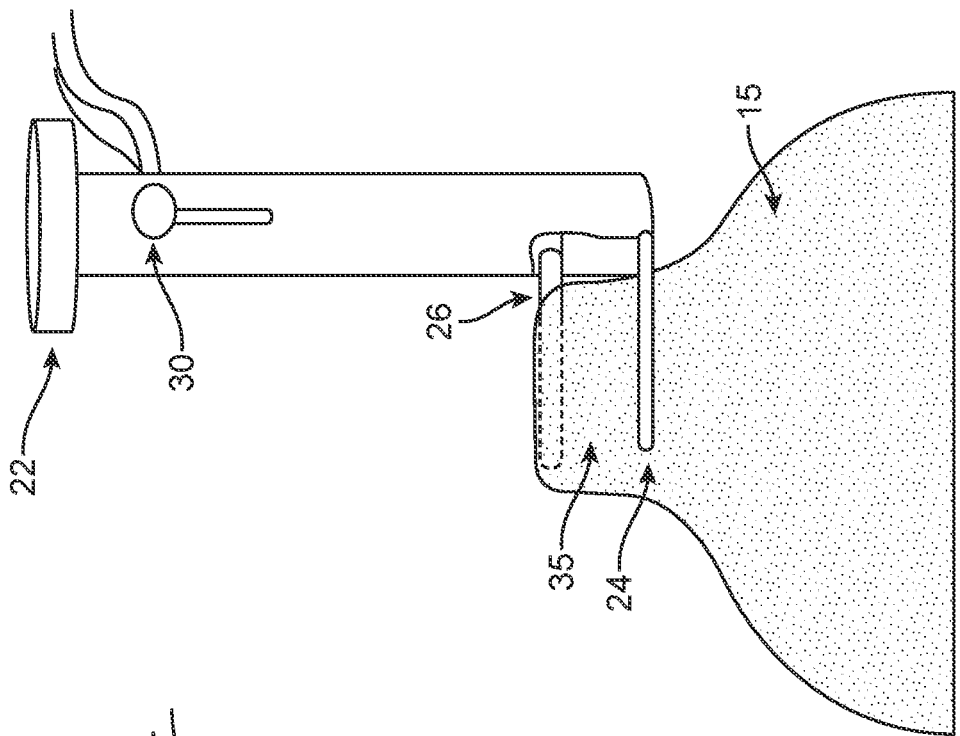
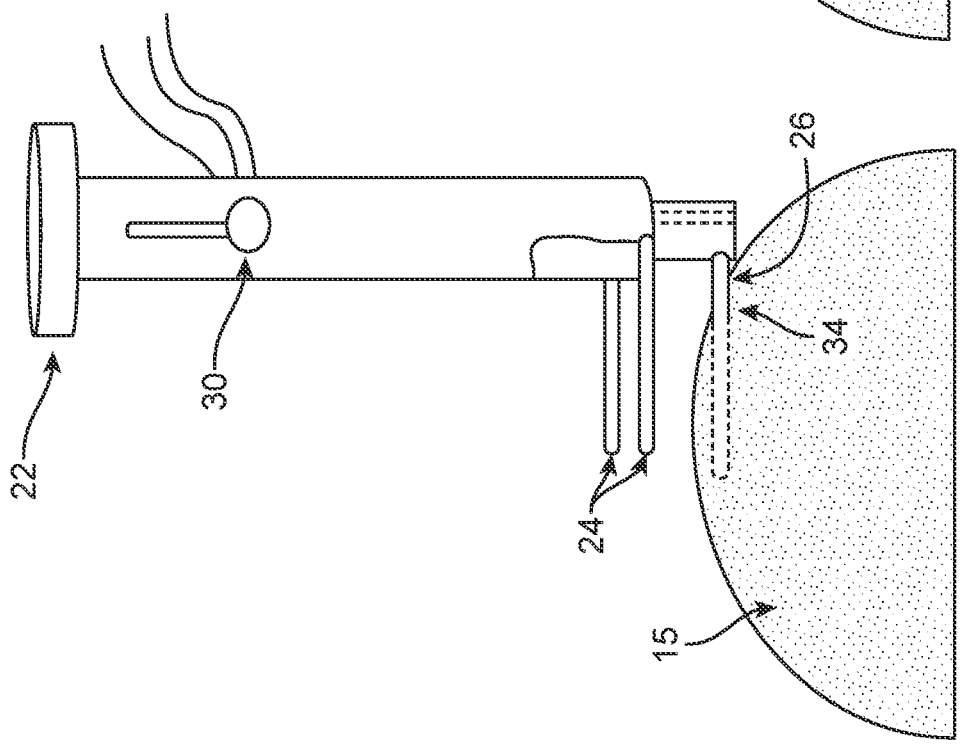
FIG. 12A
FIG. 12B

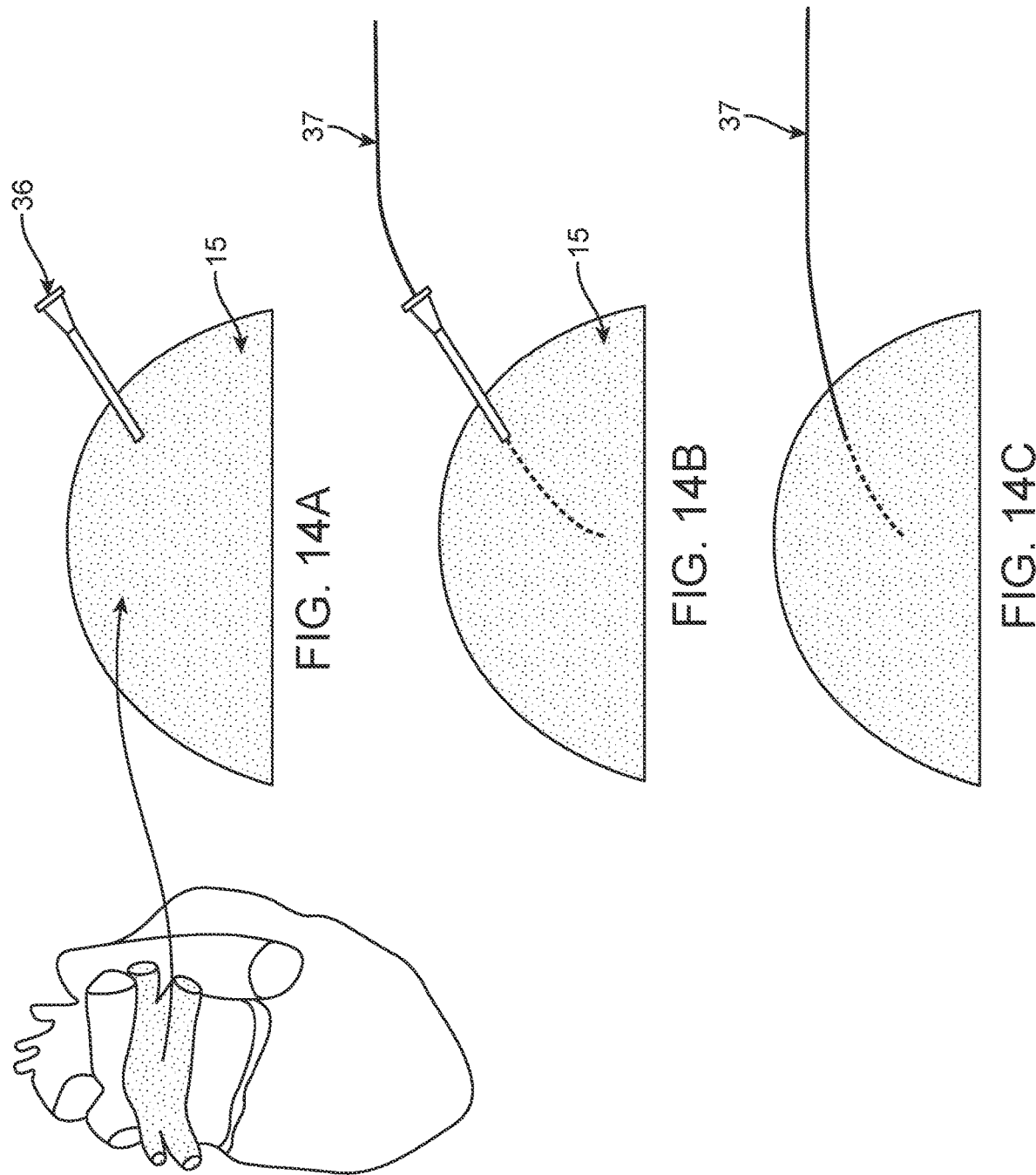

PURSESTRING SUTURE RETRACTOR AND METHOD OF USE

CROSS-REFERENCE

This application is a continuation of PCT Application No. PCT/US2019/012538, filed Jan. 7, 2019, entitled "PURSESTRING SUTURE RETRACTOR AND METHOD OF USE"; which claims the benefit of U.S. Provisional Application No. 62/614,326, filed Jan. 5, 2018, entitled "PURSESTRING SUTURE RETRACTOR AND METHOD OF USE", the entire contents of which are incorporated herein by reference.

TECHNICAL FIELD

This disclosure relates generally to devices, systems, and methods for preparing a hollow organ, remote from the site of a surgical skin incision, for the entry of instruments to perform a surgical procedure inside the organ, and for closure of the hollow organ upon completion of the surgical procedure.

BACKGROUND

Many surgical procedures are commonly performed within a hollow organ or biological structure, such as the stomach or the heart, of a patient. An incision may be placed in an outer surface of the hollow organ to provide for passage of instruments needed to perform the surgical procedure. Such surgical procedures, when performed in a minimally-invasive manner may be initiated through a small skin incision, which may be remote to the hollow organ. The surgical instrument may be inserted into the body of the patient through the skin incision and advanced into the hollow organ via the incision therein. Once at the hollow organ, a seal must not only be created between the incision in the hollow organ and the operative instrument during the surgical procedure, but the incision must also be closed upon completion of the procedure, to prevent loss of internal contents of the organ into the surrounding tissue. For example, it is deleterious to allow leakage of caustic acidic stomach contents into the abdominal cavity while performing a surgical procedure on the stomach. If the surgical procedure involves entry into the heart, control and subsequent closure of the heart access incision can be particularly important, as positive blood pressure in the chambers of the heart causes hemorrhage, which can lead to patient death if uninhibited blood loss occurs.

Introduction of one or more medical devices through the wall of the hollow organ and into a hollow organ is generally accomplished by placement of a pursestring suture in the wall of the hollow organ. An incision is then performed in the center of the pursestring suture, to allow entry of a cannula or other instrument access to the interior of the hollow organ. The pursestring is cinched tight around the device to prevent loss of the internal contents of the organ during performance of the surgical procedure in the interior of the hollow organ. At the conclusion of the procedure, the pursestring suture is cinched down completely, and tied to permanently close the incision in the organ wall. For example, if the hollow organ is the heart, a pursestring suture may be placed in the heart wall before making an incision to allow access to one or more chambers of the heart. The surgical instrument may be inserted into the heart through the incision and the pursestring may be cinched tight to maintain hemostasis and prevent blood loss around the device during performance of the surgical procedure in the interior of the heart. After the procedure, the surgical device may be removed and the pursestring suture may be cinched further to close the incision.

Placement of the pursestring suture may be performed using a surgical needle holder to grasp a curved needle with the attached suture used to form the pursestring. The jaws of the needle holder grasp the curved needle near the central portion of its arc. Proper surgical technique requires insertion of the needle tip perpendicular to the surface of the tissue, followed by rotation of the needle holder to drive the needle through both sides of the tissue wall, which can require significant working space adjacent the hollow organ in order to allow for movement and rotation of the needle holder. Pursestring suture placement is therefore easily performed when the hollow organ is fully exposed, for example when the heart is completely exposed during open heart surgery.

However, pursestring suture placement is significantly more difficult, if not impossible, when the hollow organ is accessed in a manner which does not significantly expose the hollow organ to the operating field, such as during minimally-invasive procedures which provide access via a small incision in the skin. For example, if the heart is accessed via a small suprasternal anterior neck incision, such as may be used in a mediastinoscopic approach, pursestring suture placement using conventional methods becomes very difficult. With such an approach, access to the heart from the neck incision is performed through a narrow tunnel which allows for a limited range of motion of the needle holder. The needle holder is generally positioned orthogonal to the plane of the curved needle during suture placement. Given the constraints of the access method, it is nearly impossible to grasp a curved needle in the proper configuration, advance the needle down the long narrow tunnel, and place the needle through the wall of the heart located at the bottom of the tunnel, without significantly deforming the wall and potentially causing laceration or injury to the heart.

SUMMARY

Accordingly, there is a need for systems, methods, and devices that enable access to an interior of a hollow organ in a minimally-invasive manner when the access route provides limited instrumental range of motion. For example, when the hollow organ is a heart, access to the heart may be obtained through a small incision in the skin remote from the heart, via an anterior neck incision for example, and the working area for instrument access to the interior of the heart may be enhanced by the systems, methods, and devices described herein. There is a further need to provide systems, methods, and devices configured to minimize the loss of the internal contents of the hollow organ, e.g. blood in the case of the heart.

Some or all of the above deficiencies and other problems associated with conventional devices and methods may be reduced or eliminated by the disclosed devices and methods.

In accordance with some embodiments, a pursestring suture retractor device and method is described that allows pursestring suture placement in confined and narrow anatomic situations, more specifically in mediastinoscopic access to the heart. The retractor device retracts and reshapes the wall of the heart to facilitate suture placement for instrument access and incision closure following the surgical procedure. Deployment of the device creates opposing vertical laterally-facing walls in the heart muscle that allows a surgical needle holder aligned axially along the mediastinal access tunnel to easily place a curved needle through the heart wall to create a pursestring suture or to place interrupted sutures along the planned incision line. The retractor device may also incorporate suction capability to clear the surgical field of blood, and it may further contain a cautery electrode to form an incision in the desired location in the retracted heart muscle.

In accordance with some embodiments, the retractor device may include at least two elongated shafts which are coupled together so as to be longitudinally movable relative to each other. The shafts may be arranged in a parallel, concentric, or other suitable arrangement. An internal member is coupled to a distal end of a first shaft so as to extend therefrom in a transverse direction. A pair of external members are coupled to a distal end of a second shaft so as to extend therefrom in a direction parallel to the transverse direction. The external members are spaced apart from each other, and, by moving the first shaft relative to the second shaft, the internal member is movable relative to the external members along a plane extending longitudinally between the external members.

In specific embodiments, the endoscopic tissue retraction device includes a first shaft and a second shaft slidably coupled to the first shaft and longitudinally movable relative thereto. An internal member is coupled to the first shaft so as to extend therefrom in a transverse direction. The internal member is configured for advancement through a penetration in a target tissue of a patient. The internal members has a proximally-facing surface configured to atraumatically engage a distal surface of the target tissue after being advanced therethrough. A pair of external members are each coupled to the second shaft so as to extend therefrom generally parallel to the transverse direction. The external members are spaced apart and each having a distally-facing surface configured to atraumatically engage a proximal surface of the target tissue. The internal member is movable longitudinally relative to the external members between a distal position and a proximal position along a plane extending between the external members. The internal member is configured to apply traction to the target tissue when retracted from the distal position towards and past the pair of external members to the proximal position. The pair of external members are configured to apply counter-traction to the target tissue on opposing lateral sides of the internal member, whereby the target tissue is re-shaped so as to have a pair of laterally facing surfaces each extending between the internal member and one of the external members.

In accordance with some embodiments, the first shaft may be rigid.

In accordance with some embodiments, the first shaft may comprise a high durometer polymer material or metal. The first shaft may comprise polycarbonate, liquid crystal plastic, nylon, PTFE, ABS, polypropylene, titanium, or stainless steel.

In accordance with some embodiments, the second shaft may be rigid.

In accordance with some embodiments, the second shaft may comprise a high durometer polymer material or metal. The second shaft may comprise polycarbonate, liquid crystal plastic, nylon, PTFE, ABS, polypropylene, titanium, or stainless steel.

In accordance with some embodiments, the second shaft may be configured to be inserted into a working channel of a surgical instrument, an endoscope, a mediastinoscope, or a suprasternal access device placed through an opening in the body of the body of the patient.

In accordance with some embodiments, the first shaft may be slidably disposed within at least a portion of the second shaft.

In accordance with some embodiments, the internal member may be rigid.

In accordance with some embodiments, the internal member may comprise stainless steel.

In accordance with some embodiments, the target tissue may be a wall of a heart of the patient. The internal member may be configured to be advanced through the wall of the heart while the heart is beating. Alternatively or in combination, the internal member may be configured to apply traction to the target tissue while the heart is beating. Alternatively or in combination, the internal member may be configured to be advanced through the wall of the heart while a chest of the patient remains closed. Alternatively or in combination, the internal member may be configured to apply traction to the target tissue while a chest of the patient remains closed.

In accordance with some embodiments, the internal member may be configured to be positioned about 1 cm proximal to the pair of external members when in the proximal position.

In accordance with some embodiments, the internal member may be configured to be movable from a longitudinal configuration to a transverse configuration. The internal member may be configured to engage the distal surface of the target tissue when in the transverse configuration. Optionally, the internal member may be rotatably movable from the longitudinal configuration to the transverse configuration. For example, the internal member may be configured to be rotated from the longitudinal configuration to the transverse configuration in response to a force applied to the internal member in the longitudinal configuration.

In accordance with some embodiments, the internal member may comprise a pivoting joint. The device may further comprise a rigid element coupled to the internal member and configured to apply force to the internal member to maintain the internal member in the longitudinal configuration when compressed. Tensioning of the rigid element may move the rigid elements at least a first distance and may remove the force applied to the internal member to actuate the internal member from the longitudinal configuration to the transverse configuration. The first distance may be within a range of about 1 mm to about 20 mm.

Alternatively or in combination, the device may further comprise a locking mechanism coupled to the internal member and configured to maintain the internal member in the longitudinal configuration. Disengaging the internal member from the locking mechanism may actuate the internal member from the longitudinal configuration to the transverse configuration. The locking mechanism may comprise a detent in a pivoting joint of the internal member. The detent may be configured to disengage from the internal member in the longitudinal configuration when a force within a range of about 0.10 to about 1 pounds is applied to the internal member. Optionally, the locking mechanism may further comprise a wire actuator shaped to correspond to the detent.

Alternatively or in combination, the device may further comprise a locking mechanism coupled to the internal member and configured to maintain the internal member in the transverse configuration. Disengaging the internal member from the locking mechanism may actuate the internal member from the transverse configuration to the longitudinal configuration. The locking mechanism may comprise a detent in a pivoting joint of the internal member. The detent may be configured to disengage from the internal member in the transverse configuration when a force within a range of about 2 to about 5 pounds is applied to the internal member.

In accordance with some embodiments, the internal member may comprise a hollow shaft or hollow tube.

In accordance with some embodiments, the internal member may comprise a tapered distal end.

In accordance with some embodiments, a distal tip of the internal member may be tapered to sharpened to facilitate advancement through the target tissue.

In accordance with some embodiments, the internal member may comprise a guidewire lumen configured to slidably receive a guidewire therethrough. The internal member may comprise an elastomeric seal disposed within the guidewire lumen and configured to seal the target tissue and prevent fluid flow through the guidewire lumen.

In accordance with some embodiments, the internal member may comprise a flare configured to contact the target tissue while the internal member engages the distal surface of target tissue to inhibit leakage of blood or bodily fluids.

In accordance with some embodiments, the internal member may be configured to apply electrocautery energy to the target tissue to make a penetration therein. The internal member may comprise an electrode coupled thereto. Alternatively or in combination, the internal member may comprise an electrically-conductive material.

In accordance with some embodiments, the pair of external members may be rigid.

In accordance with some embodiments, the pair of external members may comprise stainless spring steel.

In accordance with some embodiments, the pair of external members may be moveable from a longitudinal configuration to a transverse configuration. The pair of external members may be configured to engage the proximal surface of the target tissue when in the transverse configuration. The pair of external members may configured to be rotated from the longitudinal configuration to the transverse configuration. For example, each of the pair of external members comprises a pivoting joint. Alternatively or in combination, the pair of external members may be configured to be rotated from the longitudinal configuration to the transverse configuration in response to a force applied to the pair of external members when in the longitudinal configuration.

Optionally, the device may further comprise at least two rigid elements coupled to the pair of external members, respectively, and configured to apply force to the pair of external members to maintain the pair of external members in the longitudinal configuration when compressed. Tension on the at least two rigid elements may move the at least two rigid elements at least a first distance and may remove the force applied to the pair of external members to actuate the pair of external members from the longitudinal configuration to the transverse configuration. The first distance may be within a range of about 1 mm to about 20 mm.

Alternatively or in combination, the device may further comprise at least two locking mechanisms coupled to the pair of external members, respectively, and configured to maintain the pair of external members in the longitudinal configuration. Disengaging the pair of external members from the pair of locking mechanisms may actuate the pair of external members from the longitudinal configuration to the transverse configuration. Each of the at least two locking mechanisms may comprise a detent in a pivoting joint of each of the pair of external members. The detent may be configured to disengage from the external member in the straightened configuration when a force within a range of about 0.10 to about 1 pounds is applied to the external member. Optionally, each of the at least two locking mechanisms may comprise a wire actuator shaped to correspond to the detent.

Alternatively or in combination, the device may further comprise at least two locking mechanisms coupled to the pair of external members, respectively, and configured to maintain the pair of external members in the transverse configuration. Disengaging the pair of external members from the at least two locking mechanisms may actuate the pair of external members from the transverse configuration to the longitudinal configuration. Each of the at least two locking mechanisms may comprise a detent in a pivoting joint of each of the pair of external members. The detent may be configured to disengage from the external member in the transverse configuration when a force within a range of about 2 to about 5 pounds is applied to the external member.

In accordance with some embodiments, the pair of external members may comprise at least two wire extensions.

In accordance with some embodiments, the first shaft may be configured to translate relative to the second shaft. Translation of the first shaft relative to the second shaft may actuate the internal member from the distal position to the proximal position. Optionally, the second shaft may comprise at least two slots disposed in opposing walls of a proximal end of the second shaft and the first shaft may comprise a crossbar configured to extend through the at least two slots. Translation of the crossbar within the slots may translate the first shaft relative to the second shaft.

In accordance with some embodiments, the first shaft may comprise a suction lumen configured to remove blood or bodily fluids from the target tissue. Optionally, the suction lumen may be configured to be fluidly coupled to a negative pressure source.

In accordance with some embodiments, a system includes any of the devices described herein and a guidewire slidably disposed in a lumen of the internal member. Optionally, the internal member may be configured to be advanced through the target tissue over the guidewire.

In accordance with some embodiments, a system includes any of the devices described herein, one or more sutures, and a curved needle coupled to the one or more sutures and configured to place the one or more sutures in the target tissue when the internal member applies traction to the target tissue. The curved needle may configured to place the one or more sutures in the target tissue as a pursestring suture. Alternatively or in combination, the curved needle may be configured to place the one or more sutures in the target tissue as a plurality of interrupted sutures.

In accordance with some embodiments, a system includes any of the devices described herein and a visualization device. The visualization device may comprise a mediastinoscope, a camera coupled to a distal portion of the endoscopic tissue retraction device, an optical channel in the endoscopic tissue retraction device, or an endoscope.

In accordance with some embodiments, a method of placing a suture in a tissue of a patient includes inserting an endoscopic tissue retraction device into a body of a patient and advancing a distal portion of the endoscopic tissue retraction device toward a target tissue of the patient, the distal portion comprising an internal member and a pair of spaced-apart external members, the internal member being longitudinally movable relative to the pair of external members along a plane extending between the pair of external members. The method further includes advancing the internal member of the tissue retraction device through the target tissue to engage a distal surface of the target tissue and applying traction to the target tissue with the internal member by retracting the internal member from a distal position towards and past the pair of external members to a proximal position while engaging a proximal surface of the target tissue with the pair of external members. The pair of external members are configured to apply counter-traction on opposing lateral sides of the internal member, wherein the target tissue is re-shaped so as to have a pair of laterally facing surfaces each extending between the internal member and one of the external members. The method further includes placing one or more sutures in at least one of the laterally facing surfaces of the target tissue while the internal member and the pair of external members apply traction thereto.

In accordance with some embodiments, the method may further comprise making an incision in the target tissue within the one or more sutures. Making the incision may comprise applying electrocautery energy to the target tissue with the internal member. Alternatively or in combination, making the incision may comprise cutting the target tissue with a blade. Alternatively or in combination, making the incision may comprise advancing a cardiovascular sheath and dilator through the target tissue and dilating the target tissue with the dilator.

In accordance with some embodiments, the method may further comprise closing the incision by tightening or knotting the one or more sutures around the incision. Placing one or more sutures in the target tissue may comprise placing a pursestring suture and tightening the one or more sutures may comprise cinching the pursestring suture. Alternatively or in combination, placing one or more sutures in the target tissue may comprise placing a plurality of interrupted sutures and knotting the one or more sutures may comprise knotting the plurality of interrupted sutures.

In accordance with some embodiments, the method may further comprise inserting a distal portion of a surgical instrument through the incision. The method may further comprise sealing the incision around the surgical instrument to inhibit leakage of blood or bodily fluids. Sealing the incision around the surgical instrument may comprise tightening or knotting the one or more sutures around the incision.

In accordance with some embodiments, the method may further comprise removing the distal portion of the surgical instrument from the incision and closing the incision after removing the distal portion of the surgical instrument by tightening or knotting the one or more sutures around the incision. Placing one or more sutures in the target tissue may comprise placing a pursestring suture and tightening the one or more sutures may comprise cinching the pursestring suture. Alternatively or in combination, placing one or more sutures in the target tissue may comprise placing a plurality of interrupted sutures and knotting the one or more sutures may comprise knotting the plurality of interrupted sutures.

In accordance with some embodiments, the method may further comprise performing a surgical procedure with the surgical instrument after the surgical instrument is inserted through the incision. The target tissue may comprise a wall of a heart of the patient and wherein the surgical procedure comprises at least one of mitral valve replacement, mitral valve repair, mitral annuloplasty, chordal repair, chordal replacement, leaflet resection, or leaflet coaptation. Alternatively or in combination, the target tissue may comprise a wall of a heart of the patient and wherein the surgical procedure comprises at least one of atrial appendage closure, atrial ablation, pulmonary vein ablation, septal defect closure, aortic valve repair, aortic valve replacement, tricuspid valve repair, tricuspid valve replacement, implantable cardiac defibrillator (ICD) implantation, pacemaker implantation, or placement of leads for ICD's or pacemakers, myocardial biopsy, or septectomy.

In accordance with some embodiments, the target tissue may comprise a wall of a heart of the patient. In some embodiments, the heart may remain beating during the steps of inserting the endoscopic tissue retraction device, advancing the distal portion, advancing the internal member, applying traction, and placing the one or more sutures. Alternatively or in combination, a chest of the patient may remain closed during the steps of inserting the endoscopic tissue retraction device, advancing the distal portion, advancing the internal member, applying traction, and placing the one or more sutures.

In accordance with some embodiments, placing the one or more sutures may comprise placing a pursestring suture. Alternatively or in combination, placing the one or more sutures may comprise placing a plurality of interrupted sutures.

In accordance with some embodiments, advancing the internal member may be configured to create a penetration in the target tissue through which it is advanced. Optionally, the method may further comprise delivering electrocautery energy to the target tissue from the internal member to create the penetration.

In accordance with some embodiments, the method may further comprise moving the internal member from a longitudinal configuration to a transverse configuration after it is advanced through the target tissue. Moving the internal member from the longitudinal configuration to the transverse configuration may comprise rotating the internal member from the longitudinal configuration to the transverse configuration. Rotating the internal member may comprise applying force to the internal member in the longitudinal configuration.

In accordance with some embodiments, the endoscopic tissue retraction device may comprise a rigid element coupled to the internal member and configured to apply force to the internal member to maintain the internal member in the longitudinal configuration when compressed. Moving the internal member may comprise tensioning the rigid element to remove the force applied to the internal member.

Alternatively or in combination, the endoscopic tissue retraction device may comprise a locking mechanism coupled to the internal member and configured to maintain the internal member in the longitudinal configuration. Moving the internal member may comprise disengaging the internal member from the locking mechanism.

In accordance with some embodiments, the method may further comprise moving the pair of external members from a longitudinal configuration to a transverse configuration. Moving the pair of external members from the longitudinal configuration to the transverse configuration may comprise rotating the two or more external members from the longitudinal configuration to the transverse configuration. Rotating the pair of external members may comprise applying force to the pair of external members in the longitudinal configuration.

In accordance with some embodiments, the endoscopic tissue retraction device may comprise two or more rigid elements coupled to the pair of external members, respectively, and configured to apply force to the pair of external members to maintain the pair of external members in the longitudinal configuration when compressed. Moving the pair of external members may comprise tensioning the two or more rigid elements to remove the force applied to the pair of external members.

Alternatively or in combination, the endoscopic tissue retraction device may comprise two or more locking mechanisms coupled to the pair of external members and configured to maintain the pair of external members in the longitudinal configuration. Moving the pair of external members may comprise disengaging the pair of external members from the two or more locking mechanisms.

In accordance with some embodiments, inserting the endoscopic tissue retraction device into the body of the patient may comprise inserting the endoscopic tissue retraction device in a working channel of a surgical instrument, an endoscope, a mediastinoscope, or a suprasternal access device placed through an opening in the body of the body of the patient.

In accordance with some embodiments, the method may further comprise sealing the target tissue with the internal member while it engages the distal surface of the target tissue to inhibit leakage of blood or bodily fluids. The method may further comprise sealing the penetration with a flared portion of the internal member while the internal member engages the distal surface of target tissue. Alternatively or in combination, the internal member may comprise a lumen and an elastomeric seal disposed therein, the elastomeric seal being configured to inhibit flow through the lumen.

In accordance with some embodiments, the method may further comprise inserting a guidewire through the target tissue before advancing the internal member therethrough. Advancing the internal member through the target tissue may comprise slidably advancing the internal member over the guidewire, the guidewire being disposed in a lumen of the internal member. The method may further comprise removing the internal member from the target tissue after the sutures are placed. Optionally, the internal member may be slidably removed over the guidewire. In some embodiments, the guidewire may remain through the target tissue after the internal member is removed.

In accordance with some embodiments, the endoscopic tissue retraction device may comprise a first shaft coupled to the internal member and a second shaft slidably coupled to the first shaft, the second shaft being coupled to the two or more external members. Retracting the internal member from the distal position to the proximal position may comprise translating the first shaft relative to the second shaft.

In accordance with some embodiments, the method may further comprise suctioning blood or bodily fluids from the target tissue through a suction lumen in the endoscopic tissue retraction device.

In accordance with some embodiments, the method may further comprise visualizing the target tissue while inserting the endoscopic tissue retraction device, advancing the distal portion, advancing the internal member, applying traction, placing the one or more sutures, or making the incision. Visualizing may comprise viewing the target tissue with a mediastinoscope, a camera coupled to the distal portion of the endoscopic tissue retraction device, an optical channel in the endoscopic tissue retraction device, or an endoscope.

In accordance with some embodiments, the target tissue may comprise a roof of the left atrium. The distal portion of the endoscopic tissue retraction device may be advanced to the roof of the left atrium from a penetration at a suprasternal access site while the sternum and ribs of the patient remain intact. Alternatively or in combination, the internal member may be advanced through the target tissue without penetrating or cutting a pericardium of the heart.

In specific embodiments, the retractor device includes a rigid outer tube with two external members, for example wire extensions, perpendicularly attached to the outer distal end of the tube, and a rigid inner tube that translates within the outer tube. An internal member with a tapered distal end may be perpendicularly attached to the distal end of the inner tube, and the tube may be configured to flare out at its attachment point to the inner tube. An elastomeric seal may be present at the proximal end of the inner lumen of the tapered internal member to seal against blood loss when a guidewire lies inside the tube, and upon removal of the guidewire. The tapered distal end of the internal member, also referred to as a perpendicularly attached tube, may allow it to be advanced along a guidewire, inserted more easily into a needle puncture site, and to dilate the puncture site while maintaining a hemostatic seal as the third tube is inserted through an outer wall of a heart and into the left atrium. The flare at the attachment point of the third tube to the inner tube further ensures that the internal member creates a seal at the puncture site, minimizing or eliminating bleeding during heart wall retraction.

In accordance with some embodiments, slots may be present in opposing walls of the proximal outer tube, and a crossbar may extend through these slots and attach to the inner tube. The crossbar may be used as a control actuator for translation of the inner tube with respect to the outer tube, and it may also serve to key the inner tube with the outer tube to prevent relative rotation between the two. The slots may be positioned so that upon full extension of the inner tube, the internal member with a tapered end lies approximately 1 cm distal to the two wire extensions on the outer tube; and upon full proximal retraction, the attached internal member on the inner tube lies approximately 1 cm proximal to the two wire extensions on the outer tube. An open channel may extend from the distal end of the inner tube to one side of the crossbar, and a vacuum tube may be attached to that side of the crossbar to allow suction to be performed by the inner tube. An insulated conductive electrode may extends down the inner tube and connect to the internal member, allowing electrocautery energy to be applied to the internal member to create an incision line in a heart wall, an atrial wall for example. The outer surface of the inner tube may be coated with a non-conductive material to avoid unintentional energy conduction to tissue outside of the incision line.

In accordance with some embodiments, the retractor device may be particularly useful in a mediastinoscopic approach to access and operate inside the left atrium of the heart, to repair the mitral valve for example. To expose the left atrium from a mediastinoscopic approach, a 6-8 cm incision may be performed in the anterior neck superior to the sternal notch, and blunt dissection may be conducted anterior to the trachea. The dissection plane may be advanced inferiorly to expose the pulmonary veins and the dome of the left atrium. These structures lie posterior to the pulmonary artery. The mediastinoscope may contain an endoscope for visualization of internal structures on a video monitor, and an elongated curved retraction blade, to maintain an operating tunnel that extends from the neck incision inferiorly to the dome of the left atrium.

In accordance with some embodiments, after the mediastinoscope has been advanced into position to expose the heart, a long needle may be advanced down the working tunnel and inserted into the dome of the left atrium. Bright red, oxygenated blood exiting the proximal hub of the needle indicates that the needle has entered the left atrium, and not the pulmonary artery that carries dark, un-oxygenated blood. A guidewire may be advanced through the needle into the left atrium, and the needle may then be removed. The tapered end of the internal member of the retractor device may be loaded onto the guidewire outside the patient's body, advanced through the mediastinal tunnel, and inserted through the needle puncture site into the left atrium. The guidewire may then be removed, the elastomeric seal maintaining hemostasis after guidewire removal. During the insertion maneuver, the two wire extensions attached to the outer tube may be situated above the surface of the left atrium. Upon actuation of the crossbar, the internal member inside the left atrium may be retracted 1 cm above the two wire extensions, thereby forming a tent in the atrial wall. The vertical laterally-facing walls of the tented atrium facilitate placement of a pursestring suture deep in the mediastinum, as the long axis of the needle holder is collinear with the bore of the operating cavity. The tip of the curved needle is easily placed perpendicular to the vertical wall of the atrial tent, and axial rotation of the needle holder is likewise easily performed to place a pursestring stitch. Upon completion of a pursestring suture, the guidewire may be reinserted through the retractor into the left atrium, the retractor removed, and a standard cardiovascular sheath and dilator advanced along the guidewire to provide access into the heart. The free ends of the suture may be pulled through a length of polymer tubing to cinch the pursestring around the cardiovascular sheath, and a surgical clamp placed on the outside of the polymer tube with its indwelling sutures, forming what is commonly known as a Rumel tourniquet. Upon completion of the surgical procedure, the polymer tube is removed, and the suture ends tied to permanently close the pursestring.

In accordance with some embodiments, if a larger incision is desired in the atrial wall, instead of cardiovascular sheath placement, electrocautery energy may be applied the internal member, causing incision of the atrial wall along a part of, or all of, the length of the internal member. Alternatively, a scalpel blade may be used to incise the atrial wall, with the intracardiac tubular structure acting as a backstop inside the heart, to avoid injury to intracardiac structures upon performance of the incision. Direct scalpel incision avoids creation of tissue char that occurs during electrocautery use, and this may be preferred by some surgeons. The retractor device may also be used to assist in the placement of a series of interrupted sutures, rather than a pursestring suture. Multiple curved needle armed sutures may be placed through both walls of the atrial tent, and the ends of the suture externalized, or brought out of the body via the neck incision. The individual sutures are tied to close the incision at the end of the procedure.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIGS. 2A-2B show the cylindrical shaped boundary of the working tunnel provided by a mediastinoscopic approach to the heart.

FIGS. 3A-3C show the steps in the placement of a pursestring suture using conventional techniques.

FIG. 5 shows that the required orientation of a needle holder during execution of a pursestring suture using conventional techniques lies far outside the boundary of the working tunnel that exists with mediastinoscopy.

FIGS. 6A-6D show various views of an endoscopic pursestring suture retractor. FIG. 6A shows a front view of the endoscopic retractor. FIG. 6B shows a side view of the endoscopic retractor. FIG. 6C shows a posterior view of the endoscopic retractor. FIG. 6D shows a tapered distal end of the endoscopic retractor.

FIGS. 12A-12C demonstrate the mechanism of retraction of the atrial wall using an endoscopic pursestring suture retractor.

FIGS. 14A-14E show placement of an endoscopic pursestring suture retractor into the left atrium of the heart. FIGS. 14A-14C show placement of a guidewire into the left atrium of the heart via a needle. FIG. 14D shows an endoscopic pursestring suture retractor loaded onto the guidewire following needle removal. FIG. 14E shows advancement of the endoscopic pursestring suture retractor along the guidewire into the left atrium of the heart.

DETAILED DESCRIPTION

Figure 1:
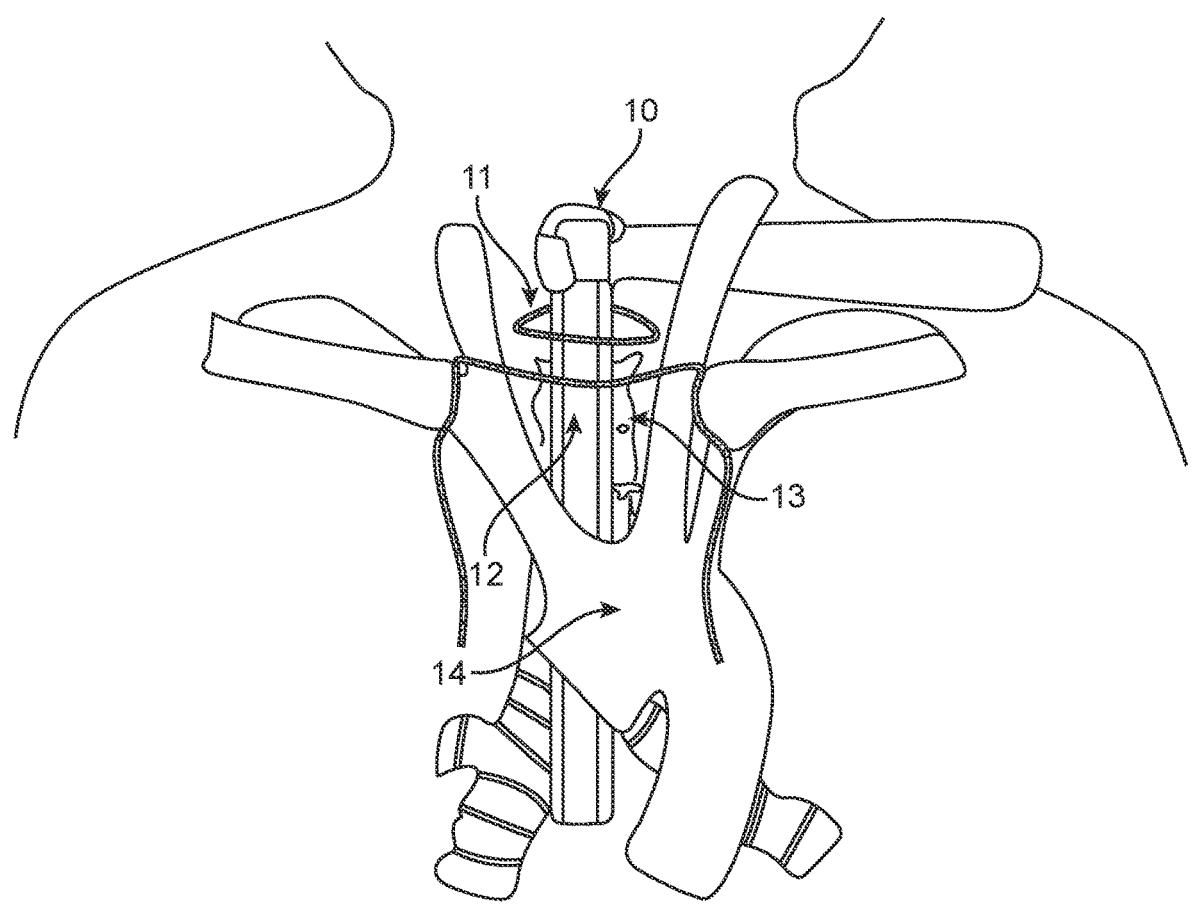
FIG. 1 shows a mediastinoscope inserted via a neck incision to access the heart.

Reference will now be made in detail to implementations, examples of which are illustrated in the accompanying drawings. In the following detailed description, numerous specific details are set forth in order to provide a thorough understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

Many modifications and variations of this disclosure can be made without departing from its spirit and scope, as will be apparent to those skilled in the art. The specific implementations described herein are offered by way of example only, and the disclosure is to be limited only by the terms of the appended claims, along with the full scope of equivalents to which such claims are entitled. It will be readily understood that the aspects of the present disclosure, as generally described herein, and illustrated in the figures, can be arranged, substituted, combined, separated, and designed in a wide variety of different configurations, all of which are explicitly contemplated herein.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments, however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The present disclosure will be described in relation to the deployment of the device for retraction of an atrial wall of the heart to aid in the placement of one or more sutures therein. However, one of skill in the art will appreciate that this is not intended to be limiting and the devices and methods disclosed herein may be used in other anatomical areas to access other hollow organs or biological structures and in other surgical procedures. Anatomical areas may, for example, include the thoracic cavity, the abdominal cavity, the neck, the back or spine, or any other anatomical area known to one of ordinary skill in the art. Hollow organs or biological structures may, for example, include the heart, the stomach, the colon, the small intestine, the bladder, the gallbladder, the bile ducts, the fallopian tubes, the ureters, the appendix, or any other hollow organ known to one of ordinary skill in the art. Procedures may, for example, include mitral valve replacement or repair, mitral annuloplasty, chordal repair or replacement, coronary artery bypass grafting, colorectal surgery, small intestine surgery, bariatric surgery, stomach surgery, or other surgical procedures which may leave require an incision for access into a hollow organ and would benefit from a minimally-invasive device and method for retracting tissue for placement of sutures around the incision.

As a non-limiting example, reference will now be made to the use of an endoscopic tissue retraction device for performing reconfiguration of the left atrial wall to facilitate the placement of a pursestring suture in a tight space remote from the entry incision site. For example, the entrance incision may be in the neck of a patient, such as in the suprasternal notch, which may allow for access to the left atrial wall via a path through the mediastinal space of the body. Such a path may be substantially similar to that travelled by a mediastinoscope or other suprasternal access device and may provide direct access to the top of the heart with minimal injury to the patient compared to open heart surgical methods which often require cutting a bone (such as the sternum, manubrium, or a rib) and/or the thoracic diaphragm, or spreading the ribs, thereby avoiding the complications associated with such injuries. Specific reference is made herein to accessing a target tissue comprising a roof of the left atrium. The endoscopic tissue retraction device may be advanced through the roof of the left atrium via a penetration at a suprasternal access site as described herein without injuring or altering the ribs and/or sternum of the patient. The endoscopic tissue retraction device may be advanced through the roof of the left atrium without penetrating or cutting a pericardium of the heart.

FIG. 1 illustrates the configuration of a conventional mediastinoscope 10 placed through a neck incision 11, and positioned above the left atrium of the heart. The neck incision 11 may lie superior to or adjacent the sternal notch 12. The suprasternal notch 12 is a generally triangular gap between the collar bones of the patient where the tissue is free from underlying bone. The incision location 11 may be within, above, or through the triangular gap of the suprasternal notch 12. The mediastinoscope 10 may be inserted through the incision 11 in the suprasternal notch 12 and advanced into the body of the patient along the trachea 13 in the anatomical plane anterior to the trachea 13 and posterior to the arch of the aorta 14 through a mediastinal space of the body toward the left atrium of the heart.

FIG. 2A shows a posterior view of a heart 15 with the left inferior pulmonary vein 16 depicted for orientation. The roof of the left atrium 15, which lies in the center of the area bounded by the pulmonary veins and does not comprise a pericardium, may be the target entry point into the left atrium 15 for a surgical procedure, for example using a mediastinoscope or a suprasternal access device as described in PCT/US2018/042171, the entire contents of which are incorporated herein by reference. FIG. 2B shows a cylindrically-shaped boundary of the working area 17 provided by a mediastinoscopic or suprasternal approach to the left atrium heart 15. By introducing a surgical instrument into the patient via the suprasternal notch, the roof of the left atrium 15 may be accessed without cutting bone or causing injury to other internal structures of the patient as described herein. However, compared to open heart access, the available working space 17 available with a suprasternal approach may provide a more limited instrumental range of motion within which to work. This open access area 17 may be surrounded by anatomical structures which would be deleterious to disrupt, thus surgical instrument access may be limited to the area defined by the top of the cylinder 17.

FIGS. 3A-3C show the steps of placing a pursestring suture 20 pattern in the left atrium 15 using a conventional technique. A suture 18 attached to a curved needle 19 may be used to place the pursestring suture 20 in the tissue wall. Proper suturing technique requires that the distal tip of the curved needle 19 be inserted into the target tissue, the left atrium 15, perpendicularly through the wall of the left atrium 15, as shown in FIG. 3A. Next, the curved needle 19 is rotated so as to incorporate a section of the target tissue, as shown in FIG. 3B. Multiple bites of tissue are performed in a roughly circular pattern to form the pursestring suture 20, as shown in FIG. 3C. A surgical needle holder (such as needle holder 21 shown in FIG. 4) may be used to grasp and manipulate the curved needle 19 to form the pursestring suture 20.

Figure 4:
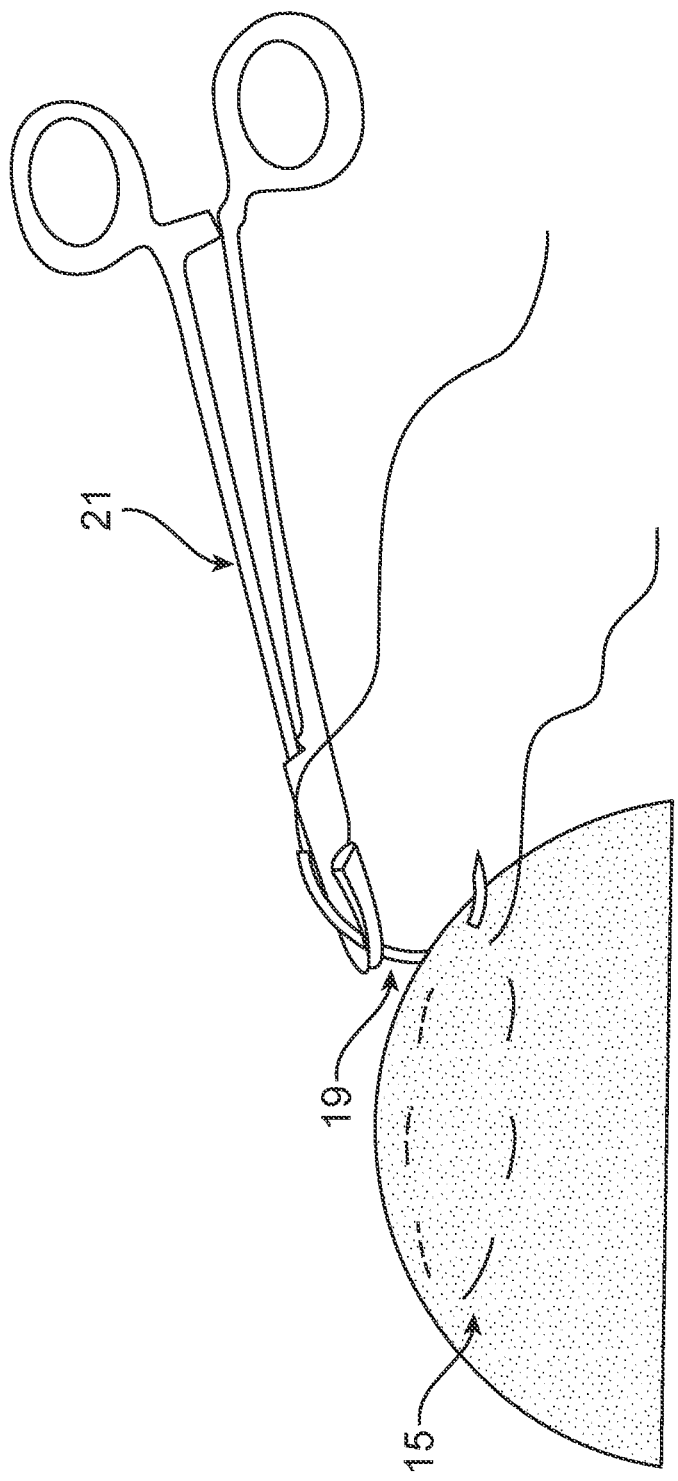
FIG. 4 shows the required orientation of a surgical needle holder during placement of a pursestring suture using conventional techniques.

FIG. 4 shows a surgical needle holder 21 grasping a curved needle 19 during placement of a pursestring suture in the left atrium 15. The surgical needle holder 21 is shown grasping the central portion of the curved needle 19 to manipulate the curved needle 19 during suture placement. The surgical needle holder 21 is typically oriented orthogonally to the central portion of the curved needle 19 when placing the suture. In order to insert the curved needle 19 perpendicular to the surface of the left atrium 15, as shown in FIG. 3A, and to rotate the curved needle 19 to place a stitch during execution of the pursestring suture as shown in FIG. 3B, the surgical needle holder 21 is thus oriented relatively parallel to the tissue surface using conventional techniques.

FIG. 5 shows that the required orientation of a needle holder 21 during execution of a pursestring suture 20 using conventional techniques lies far outside the boundary of the working tunnel 17 that exists when accessing the roof of the left atrium 15 via a mediastinoscopic or suprasternal approach path. The typical open surgical positioning of the needle holder 21 used to place a pursestring suture 20 in the left atrium 15, as shown in FIG. 4, places the handle of the needle holder 21 far outside the working space 17 available for such an approach. There is therefore a need for devices, systems, and methods to facilitate pursestring suture 20 placement when the available working space 17 does not provide for full range of motion of a needle holder 21 as would be available with more invasive access pathways.

FIGS. 6A-6D show various views of an endoscopic pursestring suture retractor 22. FIG. 6A shows a front view of the endoscopic retraction device 22. FIG. 6B shows a side view of the endoscopic retraction device. FIG. 6C shows a posterior view of the endoscopic retraction device 22. FIG. 6D shows a tapered distal end 26 of the endoscopic retraction device 22.

The endoscopic tissue retraction device 22 may comprise a first shaft 25 and a second shaft 23 slidably coupled thereto. The second shaft 23 may be longitudinally movable relative to the first shaft 25. Accordingly, the first shaft 25 may be longitudinally movable relative to the second shaft 23. In some embodiments, at least a portion of first shaft 25 may be slidably disposed within a lumen of the second shaft 23 as shown such that it translates longitudinally therein. Alternatively or in combination, at least a portion of the first shaft 25 may be slidably coupled adjacent the second shaft 23, for example in a side-by-side manner. An internal member 26 may be coupled to the first shaft 25 so as to extend therefrom in a transverse or perpendicular direction relative to a longitudinal axis of the first shaft 25 (as highlighted in FIG. 6B). A pair of external members 24 may each be coupled to the second shaft 23 so as to extend therefrom relatively parallel to the transverse direction of the internal member 26 (as highlighted in FIG. 6B). The pair of external members 24 may be spaced apart from one another and may lie in a plane disposed transverse to the longitudinal axis of the first and second shafts. In alternative embodiments, not shown, in place of second shaft 23, two separate shafts may be provided, and each external member 24 may be coupled to an individual shaft which is movable relative to the first shaft. Further, more than two external members 24 may be provided, all coupled to one shaft or each coupled to a separate shaft.

The internal member 26 may be configured to be advanced through a penetration in a target tissue into the interior of the hollow organ (e.g. the heart) as described herein. The internal member 26 may comprise a proximally-facing surface configured to atraumatically engage a distal surface of the target tissue after being advanced therethrough. The pair of external members 24 may remain outside the hollow organ when the internal member 26 is advanced therein. The pair of external members 24 may each have a distally-facing surface configured to atraumatically engage a proximal surface of the target tissue.

The internal member 26 may comprise a tapered distal end 26E. The distal end 26E may be tapered or sharpened to facilitate advancement of the internal member 26 through a target tissue as described herein. The tapered distal end 26E of the internal member 26 may allow it to be advanced along a guidewire as described herein, inserted more easily into a needle puncture site, and dilate the puncture site while maintaining a hemostatic seal as the internal member 26 is inserted through an outer wall of a heart and into the left atrium. All or a distal portion of internal member 26 may optionally be conductive and configured to deliver electrocautery energy to facilitate penetration of the target tissue, as further described below.

The internal member 26 may comprise a flare or flared portion 27 configured to contact the target tissue while the internal member 26 engages the distal surface of the target tissue to inhibit leakage of blood, bodily fluids, or other internal contents of the hollow organ. The flare 27 may be located in a proximal region of internal member 26, at or near the attachment point of the internal member 26 to the first shaft 25. When the internal member 26 is inserted into the heart wall, for example, while the heart is beating, the flare may seal the puncture site in the heart tissue such that no bleeding occurs during retraction of the heart wall.

Figure 14D:
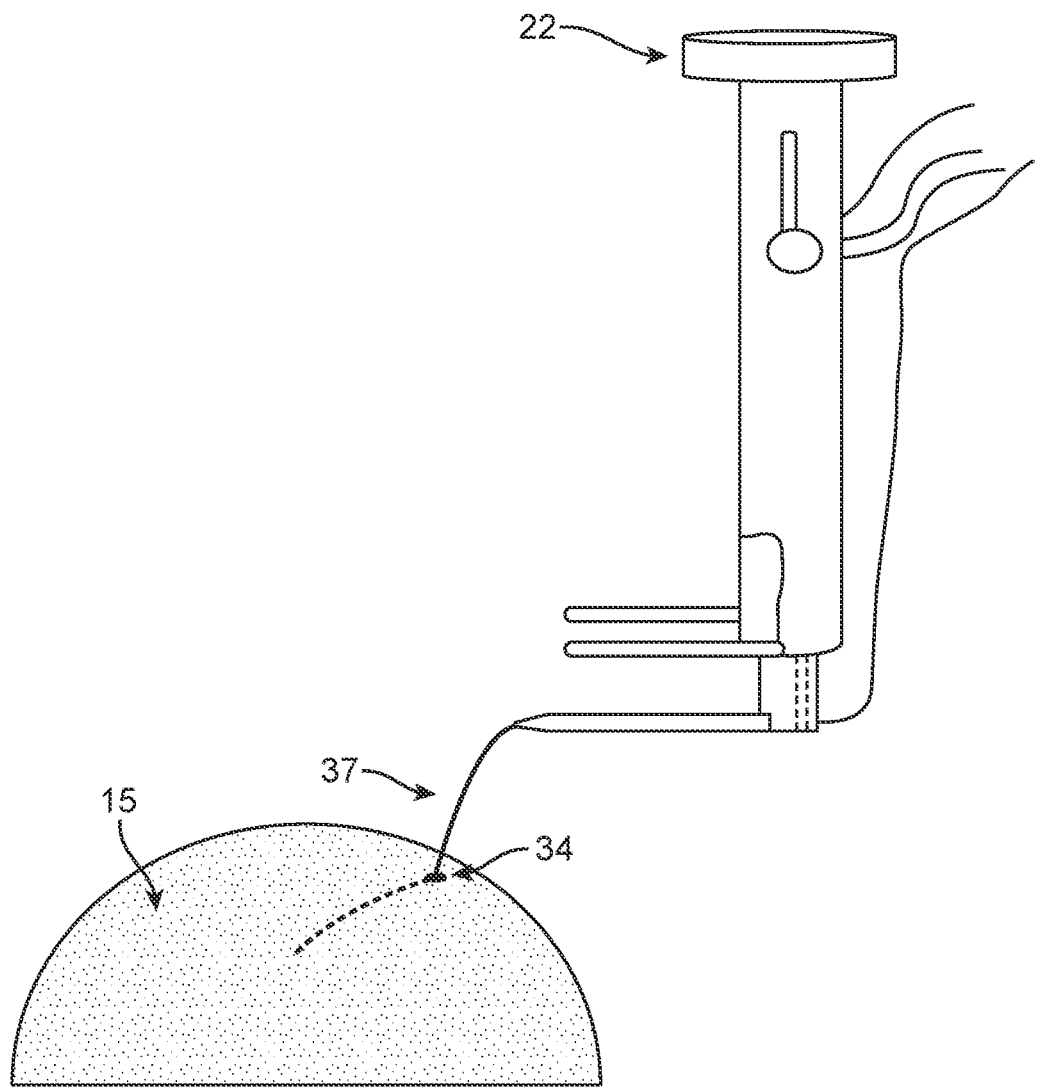
Figure 14E:
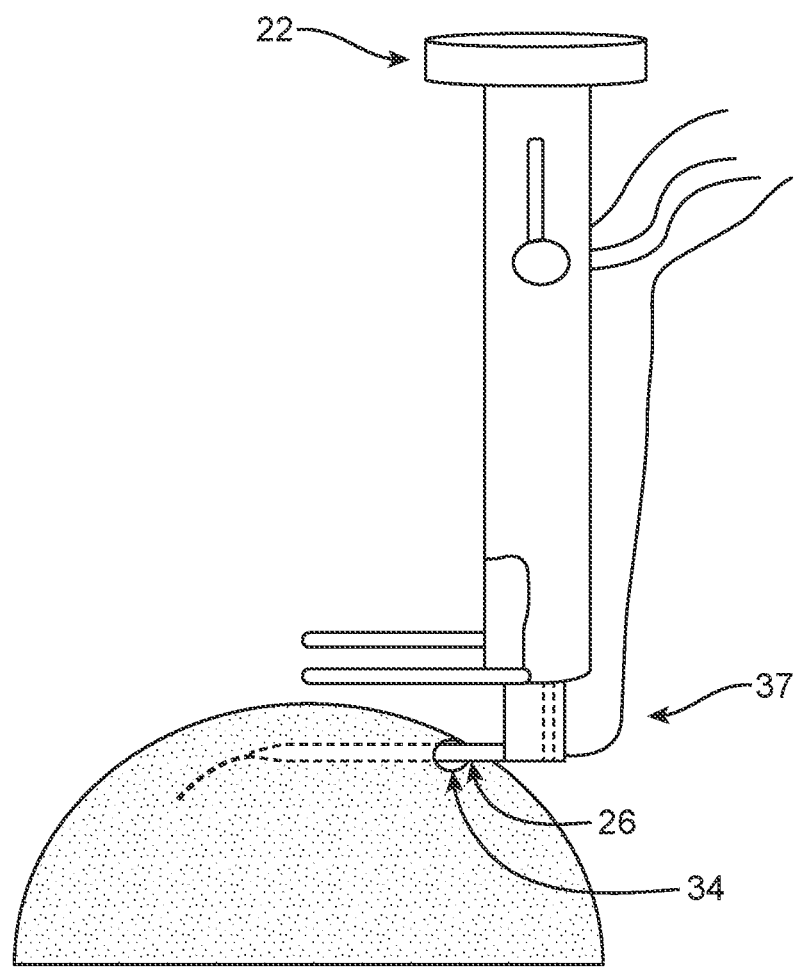

In some embodiments, the internal member 26 may comprise a lumen 29 as shown in FIG. 6D. The lumen 29 may be configured to slidably receive a guidewire therethrough (for example as shown in FIGS. 14D-14E). An elastomeric seal 28 may be disposed with the guidewire lumen 29 as shown in FIGS. 6C-6D. The elastomeric seal 28 may, for example, be positioned at a proximal end of the lumen 29. The elastomeric seal 28 may be configured to seal the target tissue when the internal member 26 is disposed therein and prevent fluid (e.g. blood or other bodily fluid) flow through the lumen 29. The elastomeric seal 28 may be configured to prevent fluid loss from the hollow organ when a guidewire is present inside the internal member 26 and when the lumen 29 is empty after removal of the guidewire.

Figure 11A:
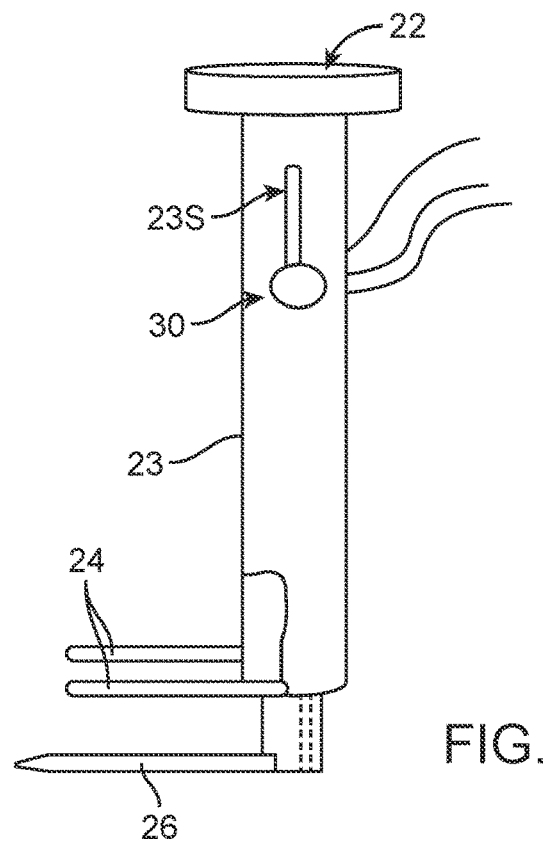
FIG. 11A shows an endoscopic pursestring suture retractor comprising an internal member in a distal configuration below two external members.
Figure 11B:
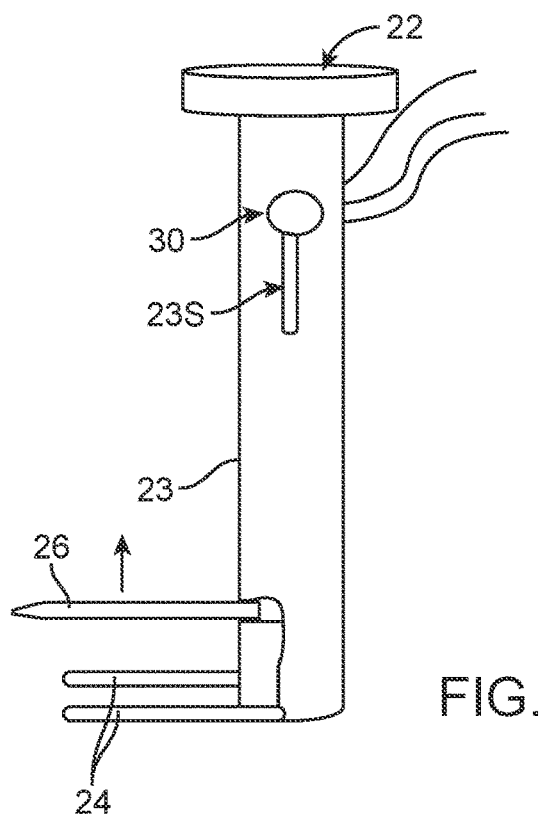
FIG. 11B shows an endoscopic pursestring suture retractor of FIG. 11A with the internal member in a proximal configuration above two external members.
Figure 12C:
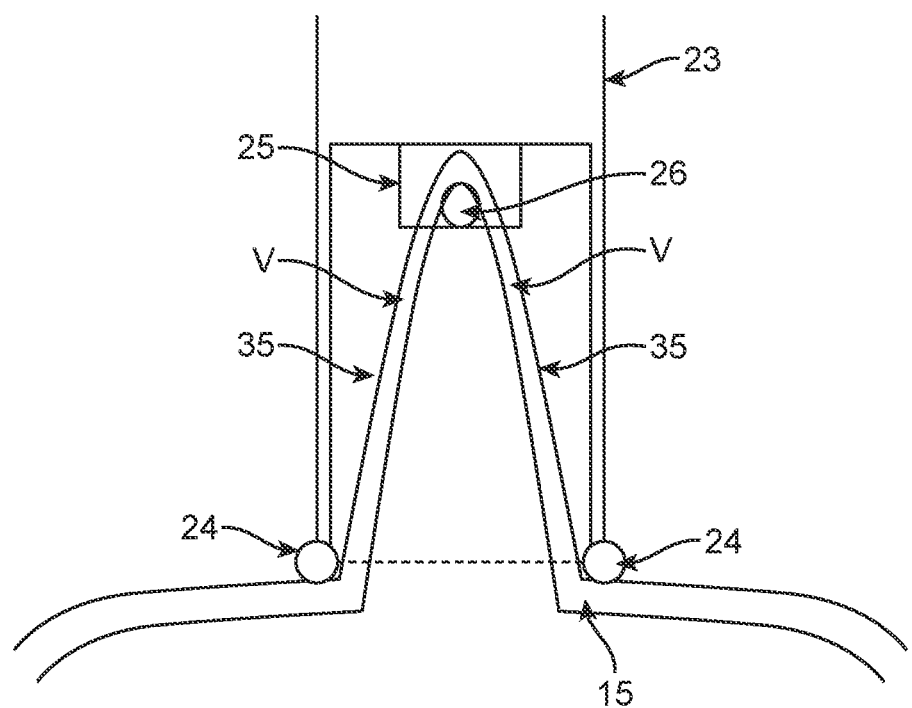

The internal member 26 may be movable longitudinally relative to the pair of external members 24 between a distal position and a proximal position along a plane longitudinally extending between the external members 26 as described herein. When retracted from the distal position, past the pair of external members 24, to the proximal positon (for example as shown in FIGS. 11A-11B), the internal member 26 may apply traction to the target tissue. The pair of external members 24 may apply counter-traction to the target tissue on opposing lateral sides of the internal member 26. The traction and counter-traction applied to the target tissue may re-shape the target tissue such that it is folded around the internal member 26 into two generally vertical portions each having a laterally-facing surface, each extending between the internal member 26 and one of the external members 24 (for example as shown in FIGS. 12B-12C). The laterally-facing surfaces may allow for suture placement, for example pursestring suture placement, for instrument access to and incision closure in a hollow organ in confined and narrow anatomic situations as described herein.

The first shaft 25 may be configured to translate relative to the second shaft 23 as described herein. Translation of the first shaft 25 relative to the second shaft 23 may actuate the internal member 26 from the distal position to the proximal position. The shafts 23, 25 may be arranged in a parallel, concentric, or other suitable arrangement.

In some embodiments, the first shaft 25 may be slidably disposed within at least a portion of the second shaft 23. The second shaft 23 may comprise at least two slots 23S disposed in opposing walls of the proximal end of the second shaft 23. The first shaft 25 may comprise a crossbar 30 configured to extend through the slots 23S. The crossbar 30 may act as the control actuator for translation of first shaft 25 with respect to the second shaft 23. Translation of the crossbar 30 within the slots 23S may translate the first shaft 25 relative to the second shaft 23 as described herein. Alternatively or in combination, the crossbar 30 may serve to key the first shaft 25 with the second shaft 23 to prevent relative rotation between the two. It will be understood by one of ordinary skill in the art that crossbar 30 and slots 23S are exemplary and are not meant to be limiting. Crossbar 30 may be substituted by any other type known in the art to control longitudinal translation of the first shaft 25 with respect to the second shaft 23, including but not limited to a rail and guide combination, friction wheel(s), electric or magnetic motor, electrically contract Nitinol® wire, and the like.

The first shaft 25 may comprise a suction lumen or open channel 31 configured to remove blood or other bodily fluids from the target tissue and the surgical field during a procedure. The suction lumen may extend from the distal end of the first shaft 25 to one side of the crossbar 30. The suction lumen 31 may be fluidly coupled to a negative pressure source, for example via a vacuum line 32 attached to the crossbar 30.

The internal member 26 may be configured to apply electrocautery energy to the target tissue to make a penetration or incision therein as described herein. The internal member 26 may be configured to create an incision in the target tissue along at least a portion of the length of the internal member 26. The internal member 26 may for example comprise an electrode. Alternatively or in combination, the internal member 26 may comprise, or may be conductively coupled to, an electrode 33E. The electrode 33E may comprise all or a portion of internal member 26, or it may comprise a separate electrode element attached to internal member 26. In some embodiments, a portion of internal member 26 may be covered with an electrically insulating material, leaving a selected portion exposed to deliver energy to tissue. A wire 33 may extend from the crossbar 30 down the first shaft 25 and connect to the internal member 26, allowing electrocautery energy to be applied to a portion of the internal member 26 to create an incision in the wall of the target tissue. The outer surface of first shaft 25 may be coated with a non-conductive material to avoid unintentional energy conduction to tissue outside of the incision line.

The internal member 26 may be coupled to the first shaft 25 at a distal end thereof. In some embodiments, the internal member 26 may comprise the distal end of the first shaft 25. In some embodiments, the internal member 26 may comprise a hollow tube or hollow shaft.

The pair of external members 24 may be coupled to the second shaft 23 at a distal end thereof. In some embodiments, the pair external members 24 may comprise the distal end of the second shaft 23. In some embodiments, the pair of external members 24 may comprise at least two wire extensions.

In some instances, at least a portion of the first shaft 25 may be rigid. For example, the entire length of first shaft 25 may be rigid. Alternatively, a distal portion of the first shaft 25 and/or a proximal portion and/or any portions therebetween may be rigid. The first shaft 25 may, for example, comprise a rigid tube or rigid solid shaft.

The first shaft 25 may be constructed of a material comprising a high durometer polymer such as polycarbonate, liquid crystal plastic, nylon, PTFE, ABS, polypropylene, or the like. Alternatively or in combination, the first shaft 25 may be constructed of a material comprising a metal such as stainless steel, titanium, or the like.

In some instances, at least a portion of the second shaft 23 may be rigid. For example, the entire length of second shaft 23 may be rigid. Alternatively, a distal portion of the second shaft 23 and/or a proximal portion and/or any portions therebetween may be rigid. The second shaft 23 may, for example, comprise a rigid tube, rigid hollow shaft. In some embodiments, for example when at least a portion of the first shaft 25 and second shaft 23 are disposed adjacent one another (instead of coaxial) the second shaft 23 may comprise a rigid solid shaft.

The second shaft 23 may be constructed of a material comprising a high durometer polymer such as polycarbonate, liquid crystal plastic, nylon, PTFE, ABS, polypropylene, or the like. Alternatively or in combination, the second shaft 23 may be constructed of a material comprising a metal such as stainless steel, titanium, or the like.

The second shaft 23 may be configured to be inserted into a working channel of a surgical instrument, an endoscope, a mediastinoscope, or a suprasternal access device, or the like placed through an opening in the body of the patient. For example, the second shaft 23 may be configured to be inserted into a working channel of a mediastinoscope or a suprasternal access device placed through an opening adjacent the suprasternal notch of the patient in order to access the roof of the left atrium of the heart.

In some instances, at least a portion of the internal member 26 may be rigid. For example, the entire length of the internal member 26 may be rigid. Alternatively, a distal portion of the internal member 26 and/or a proximal portion and/or any portions therebetween may be rigid. The internal member 26 may, for example, comprise a rigid tube or rigid solid shaft. The internal member 26 may comprise a rigid hollow tube or rigid hollow shaft.

The internal member 26 may be constructed of a material comprising a high durometer polymer such as polycarbonate, liquid crystal plastic, nylon, PTFE, ABS, polypropylene, or the like. Alternatively or in combination, the internal member 26 may be constructed of a material comprising a metal such as stainless steel, titanium, or the like.

In some instances, at least a portion of one or both of the pair of external members 24 may be rigid. For example, the entire length of one or both of the pair of external members 24 may be rigid. Alternatively, a distal portion of the internal member 26 and/or a proximal portion and/or any portions therebetween one or both of the pair of external members 24 may be rigid. One or both of the pair of external members 24 may, for example, comprise a rigid wire extension One or both of the pair of external members 24 may be constructed of a material comprising a high durometer polymer such as polycarbonate, liquid crystal plastic, nylon, PTFE, ABS, polypropylene, or the like. Alternatively or in combination, one or both of the pair of external members 24 may be constructed of a material comprising a metal such as stainless spring steel, titanium, or the like.

Figure 7A:
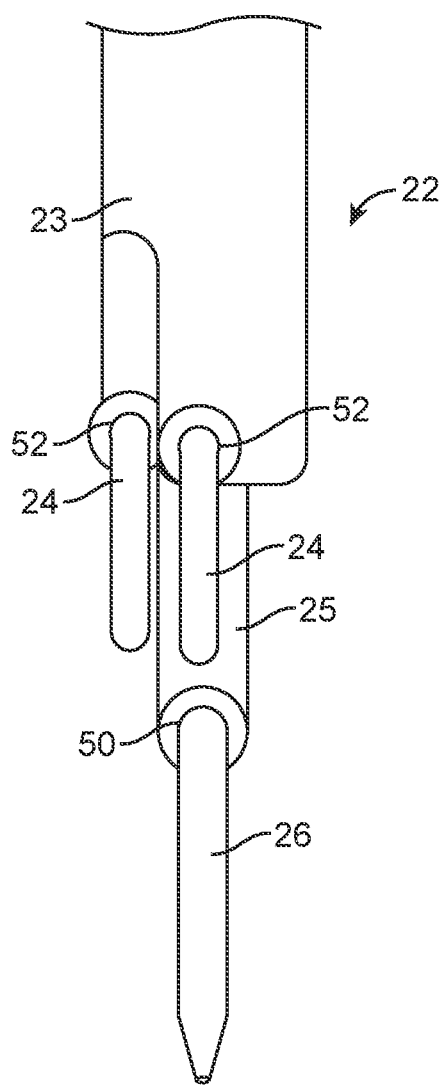
FIG. 7A shows an endoscopic retractor comprising an internal member and two external members in a longitudinal configuration.
Figure 7B:
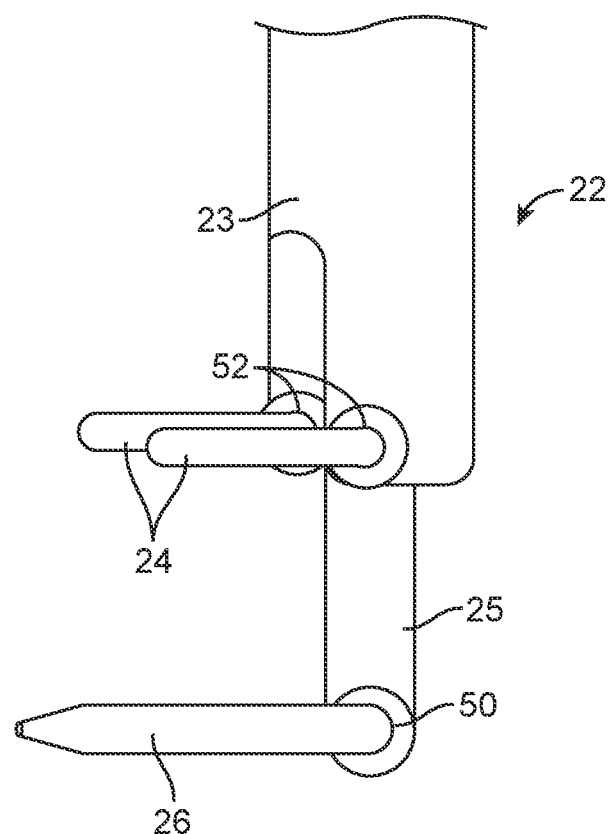
FIG. 7B shows the endoscopic retractor of FIG. 7A with the internal and external members in a transverse configuration.

FIGS. 7A-7B show an endoscopic retraction device 22 comprising an internal member 26 and a pair of external members 24. The retraction device 22 may be substantially similar to the retraction device shown in FIGS. 6A-6D, with the exception that one or more of the internal member 26 and/or one or both of the pair of external members 24 may be configured to be movable from a longitudinal configuration to a transverse configuration. FIG. 7A shows the endoscopic retractor 22 with the internal member 26 and the external members 24 in the longitudinal configuration. FIG. 7B shows the endoscopic retractor 22 with the internal member 26 and external members 24 in the transverse configuration. The internal member 26 and/or external members 24 may be advanced through the working space of the access pathway to the target tissue in the longitudinal configuration before being moved into the transverse configuration adjacent the target tissue. For example, the internal member 26 and/or external members 24 may be moved into the transverse configuration before or after the internal member 26 is advanced through the target tissue into the hollow organ as described herein. The internal member 26 may be configured to engage the distal surface of the target tissue when in the transverse configuration as described herein. The external members 24 may be configured to engage the proximal surface of the target tissue when in the transverse configuration as described herein. The longitudinal configuration of the internal member 26 and/or external members 24 may provide the retraction device 22 with a smaller profile, which may facilitate advancement and removal of the retraction device 22 through a working space, such as that provided by a mediastinoscope or suprasternal access device as described herein.

In some embodiments, the internal member 26 and/or external members 24 may be rotatably movable from the longitudinal configuration to the transverse configuration, and vice versa. The internal member 26 may, for example, comprise a pivoting joint 50 at its attachment point to the first shaft 25. Alternatively or in combination, one or both of the external members 24 may each comprise a pivoting joint 52 at their attachment points to the second shaft 23. The internal member 26 and/or external members 24 may be rotated around the pivoting joints 50, 52, respectively, in order to move the members 26, 24 between their longitudinal and transverse configurations. In some embodiments, the internal member 26 and/or external members 24 may be configured to be rotated from the longitudinal configuration to the transverse configuration in response to a force applied to the internal member 26 and/or external members 24, respectively, when in the longitudinal configuration. In some embodiments, the internal member 26 and/or external members 24 may be configured to be rotated from the longitudinal configuration to the transverse configuration in response to removal of a force applied to the internal member 26 and/or external members 24, respectively, in the longitudinal configuration. In some embodiments, the internal member 26 and/or external members 24 may be biased towards the longitudinal configuration or the transverse configuration in the absence of an applied force.

The longitudinal configuration of the internal member 26 may be substantially parallel to the longitudinal axis of the first shaft 25. The longitudinal configuration of the internal member 26 may, for example, be within about 30°, 25°, 20°, 15°, 10°, or about 5° of the longitudinal axis of the first shaft 25. The transverse configuration of the internal member 26 may be substantially perpendicular to the longitudinal axis of the first shaft 25. The transverse configuration of the internal member 26 may, for example, be within about 30°, 25°, 20°, 15°, 10°, or about 5° of a transverse axis of the first shaft 25.

The longitudinal configuration of the external members 24 may be substantially parallel to the longitudinal axis of the second shaft 23. The longitudinal configuration of the external members 24 may, for example, be within about 30°, 25°, 20°, 15°, 10°, or about 5° of the longitudinal axis of the second shaft 23. The transverse configuration of the external members 24 may be substantially perpendicular to the longitudinal axis of the second shaft 23. The transverse configuration of the external members 24 may, for example, be within about 30°, 25°, 20°, 15°, 10°, or about 5° of a transverse axis of the second shaft 23.

In some embodiments, the internal member 26 and/or one or both of the pair of external members 24 may be coupled to one or more locking mechanisms (for example one or more of the locking mechanisms shown in FIGS. 8A-10B) to maintain the members 26, 24 in the longitudinal configuration and/or transverse configuration. In some embodiments, each of the pair of external members 24 may be coupled to at least one locking mechanism. In some embodiments, disengaging the locking mechanism may actuate the internal member 26 and/or one or both of the pair of external members 24 from the longitudinal configuration to the transverse configuration. In some embodiments, disengaging the locking mechanism may actuate the internal member 26 and/or one or both of the pair of external members 24 from the transverse configuration to the longitudinal configuration. In some embodiments, one or more of the internal member 26 and/or one or both of the pair of external members 24 may comprise a plurality of locking mechanisms, for example a first locking mechanism configured to maintain the member(s) in the longitudinal configuration and a locking mechanism configuration to maintain the member(s) in the transverse configuration.

Figure 8A:
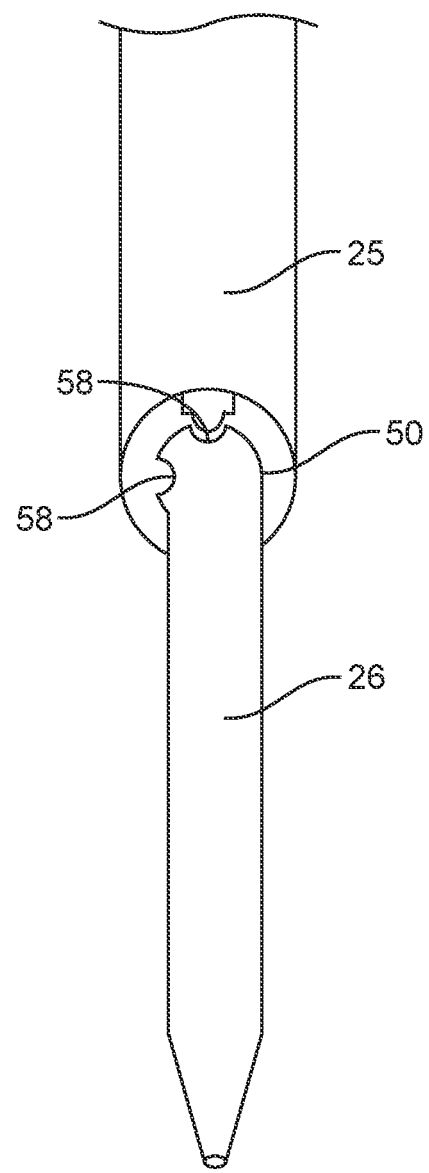
FIGS. 8A-8B show a mechanism for actuating the internal member and/or external members between a longitudinal configuration and a transverse configuration.
Figure 8B:
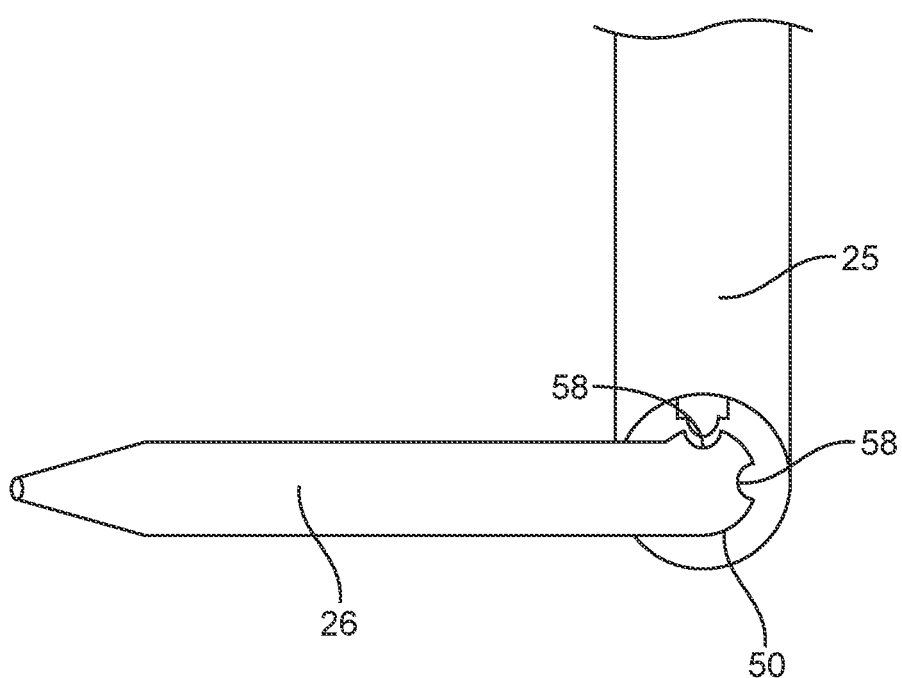

FIGS. 8A-8B show a mechanism for moving an internal member 26 and/or external members (not shown) of an endoscopic retraction device between a longitudinal configuration and a transverse configuration. The endoscopic retraction device may be substantially similar to the retraction device shown in FIGS. 7A-7B, with the exception that the internal member 26 and/or one or both of the pair of external members may be operably coupled to one or more locking mechanisms comprising one or more detents 58 in the pivoting joint 50 coupled to the internal member 26 (and/or joint 52 shown in FIGS. 7A-7B when coupled to the external members). The detents 58 may constrain the internal member 26 and/or one or both of the pair of external members in either the longitudinal configuration or the transverse configuration relative the first shaft 25 or second shaft, respectively. After being advanced through the working space in the longitudinal position as described herein, the internal member 26 and/or one or both of the pair of external members may be pivoted to and/or from the transverse configuration by applying a force to the internal member 26 and/or one or both of the pair of external members, respectively. For example, a lateral load may be placed against the distal ends of the internal member 26 and/or one or both of the pair of external members with another instrument (such as a retractor) within the working space or by an appropriately rigid and robust anatomical structure (such as a vertebral body).

In some embodiments, the internal member 26 and/or external members may be configured to be rotated from the longitudinal configuration to the transverse configuration in response to a force applied to the internal member 26 and/or external members, respectively, in the longitudinal configuration. In some embodiments, the internal member 26 and/or external members may be configured to be rotated from the transverse configuration to the longitudinal configuration in response to a force applied to the internal member 26 and/or external members, respectively, in the transverse configuration. The amount of detent 58 holding force need to maintain the internal member 26 and/or external members in the longitudinal position may be significantly less than the holding force needed to maintain the transverse position as the longitudinal position may only be used for advancement of the retraction device through the working space and little or no additional load may be placed on the pivot 50 during insertion and advancement. The detent 58 holding force needed to maintain the transverse position may be of sufficient force to maintain the transverse position while manipulating the target tissue as is described herein. For example, when in the longitudinal configuration, the detent 58 may be configured to disengage from the internal member 26 and/or external members when a force within a range of about 0.10 to about 1 pounds is applied to the internal the internal member 26 and/or external members, respectively. Alternatively or in combination, when in the transverse configuration, the detent 58 may be configured to disengage from the internal member 26 and/or external members when a force within a range of about 2 to about 5 pounds is applied to the internal the internal member 26 and/or external members, respectively.

Figure 9A:
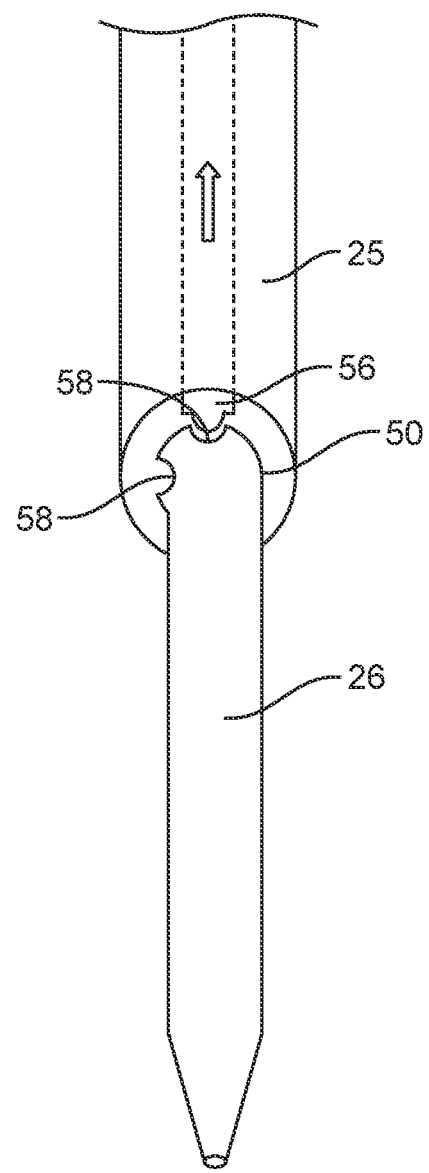
FIGS. 9A-9B show another mechanism for actuating the internal member and/or external members between a longitudinal configuration and a transverse configuration.
Figure 9B:
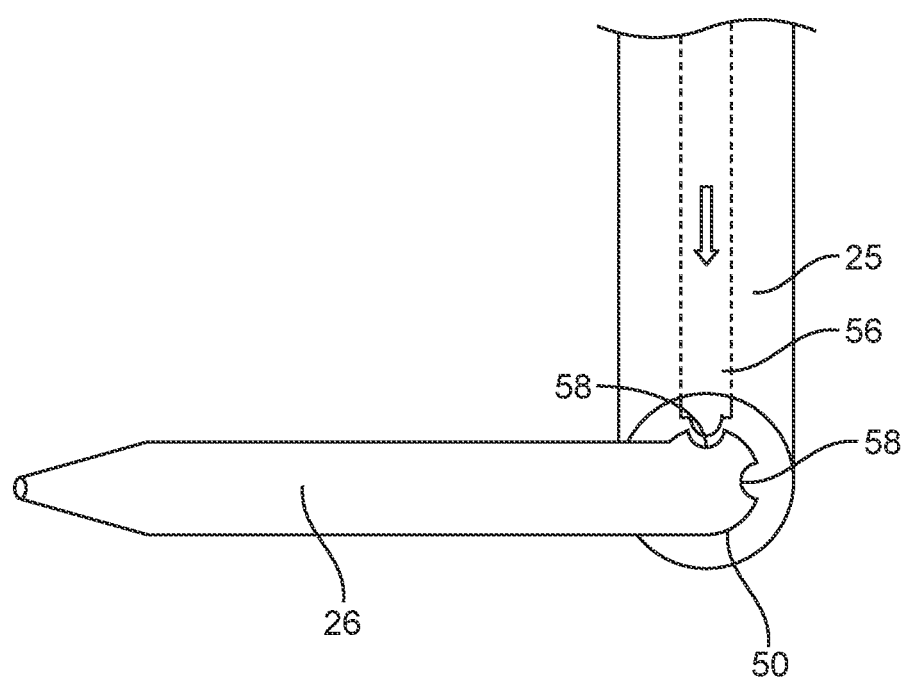

FIGS. 9A-9B show another mechanism for moving an internal member 26 and/or external members (not shown) of an endoscopic retraction device between a longitudinal configuration and a transverse configuration. The endoscopic retraction device may be substantially similar to the retraction device shown in FIGS. 7A-7B, with the exception that the internal member 26 and/or one or both of the pair of external members may be operably coupled to one or more locking mechanisms comprising one or more detents 58 and one or more wire actuators 56 to maintain the members 26, 24 in the longitudinal configuration and/or transverse configuration. Detents 58 may be substantially similar to those described in FIGS. 8A-8B. The wire actuator 56 may be slidably disposed within the first shaft 25 (or second shaft when coupled to an external member) and functionally coupled to the detent 58. Wire actuator 56 may be shaped to correspond to detent 58. The detent 58 and wire actuator 56 may constrain the internal member 26 and/or one or both of the pair of external members in either the longitudinal configuration or the transverse configuration relative the first shaft 25 or second shaft, respectively. After being advanced through the working space in the longitudinal position as described herein, the internal member 26 and/or one or both of the pair of external members may be pivoted to and/or from the transverse configuration by sliding the wire actuators 56 within the first shaft 25 or second shaft, respectively. For example, pulling on a wire actuator 56 in the direction of the hollow arrow shown in FIG. 9A may disengage the detent 58 and enable movement of the internal member 26 and/or one or both of the pair of external members from the longitudinal configuration to the transverse configuration as described herein. After disengaging the locking mechanism, a much lower level of lateral load may be required to move the internal member 26 and/or one or both of the pair of external members from the longitudinal configuration to the transverse configuration compared to the lateral load that would have been need if the wire actuator 56 mechanism were engaged with the detent 58. In some embodiments, the internal member 26 and/or one or both of the pair of external members may be biased towards a desired configuration as described herein. For example, a spring element may be included that may bias the internal member 26 and/or one or both of the pair of external members to the transverse configuration once the locking mechanism is disengaged. Pulling or pushing on the wire actuator 56 in the direction of the solid arrow shown in FIG. 9B may reengage the detent 58 and lock the internal member 26 and/or one or both of the pair of external members in a desired configuration, for example in the transverse configuration during tissue retraction.

Figure 10A:
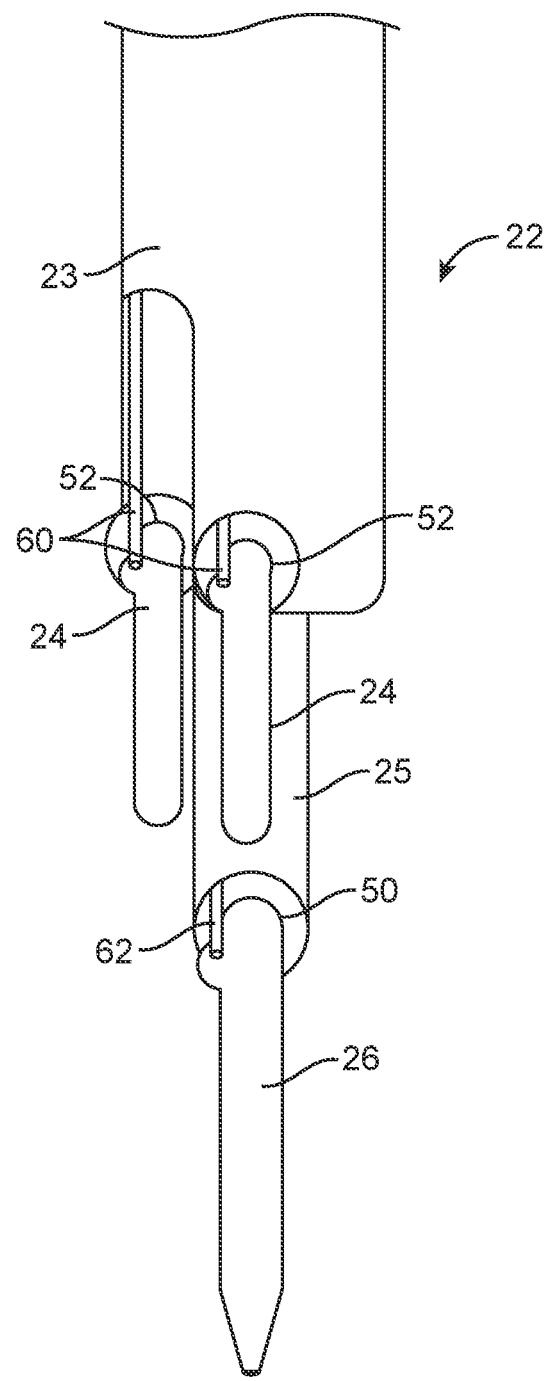
FIGS. 10A-10B show yet another mechanism for actuating the internal member and/or external members between a longitudinal configuration and a transverse configuration.
Figure 10B:
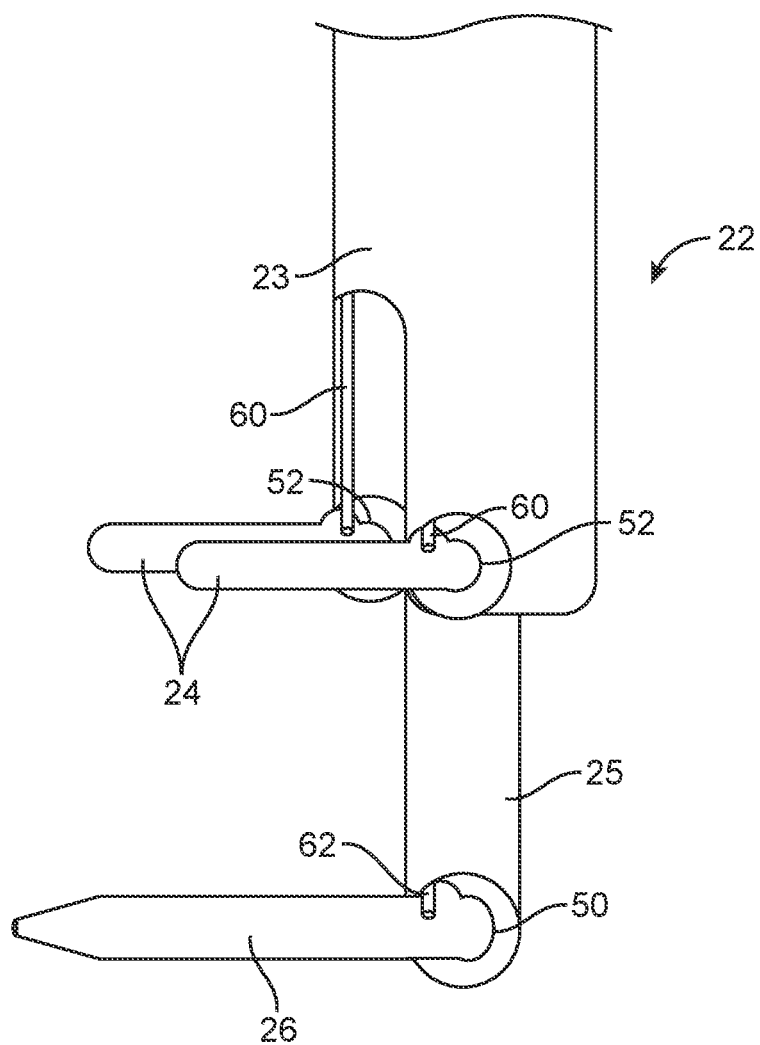

FIGS. 10A-10B show yet another mechanism for moving an internal member 26 and/or external members 24 of an endoscopic retraction device 22 between a longitudinal configuration and a transverse configuration. The endoscopic retraction device 22 may be substantially similar to the retraction device shown in FIGS. 7A-7B, with the exception that the internal member 26 and/or one or both of the pair of external members may be operably coupled to one or more locking mechanisms comprising one or more detents 58 and one or more rigid elements 60, 62 to maintain the members 24, 26, respectively, in the longitudinal configuration and/or transverse configuration. Detents 58 may be substantially similar to those described in FIGS. 8A-8B. The rigid elements 62, 60 may be operably coupled to the internal member 26 and/or one or both of the pair of external members 24, respectively. The rigid elements 62, 60 may be coupled to the internal member 26 and/or one or both of the pair of external members 24 a short distance from the pivots 50, 52, respectively. The rigid elements 60, 62 may be slidably disposed within the second shaft 23 or the first shaft 25, respectively. The rigid elements 62, 60, when compressed, may be configured to apply force to the internal member 26 and/or one or both of the pair of external members 24 to maintain the internal member 26 and/or one or both of the pair of external members 24, respectively, in the longitudinal configuration. Tensioning the rigid elements 62, 60 may move the rigid elements 62, 60 at least a first distance away from pivots 50, 52 and remove the force applied to the internal member 26 and/or one or both of the pair of external members 24 to move the internal member 26 and/or one or both of the pair of external members 24 from the longitudinal configuration to the transverse configuration. The first distance may be a small distance, for example a distance within a range of about 1 mm to about 20 mm. It will be understood by one of ordinary skill in the art that the larger the distance the rigid elements 62, 60 are tensioned, the lower the force that is needed to cause rotation.

It will be understood by one of ordinary skill in the art that any of the locking mechanisms described herein may be combined in any desired combination to provide rotation of the internal member 26 and/or external members 24 from the longitudinal position to the transverse position and vice versa. For example, in some embodiments the internal member 26 and/or external members 24 may comprise one or more detents 58 and one or more rigid elements 60, 62. In some embodiments, the internal member 26 and/or external members 24 may comprise one or more detents 58, one or more wire actuators 56, and one or more rigid elements 60, 62. In some embodiments, each of the internal member 26 and/or external members 24 may comprise the same locking mechanism. In some embodiments, one or more of the internal member 26 and/or external members 24 may comprise a different locking mechanism.

FIG. 11A shows an endoscopic pursestring suture retractor 22 having a distal portion comprising an internal member 26 in a distal configuration below (distal to) a pair of spaced-apart external members 24. The retraction device 22 may be substantially similar to any of the retraction devices described herein. FIG. 11B shows the endoscopic pursestring suture retractor 22 with the internal member 26 in a proximal configuration above (proximal to) two external members 24. The internal member 26 may be movable longitudinally relative to the pair of external members 24 between a distal position and a proximal position. The internal member 26 may be longitudinally movable along a plane of motion extending between the pair of external members 24. This plane of motion may be generally perpendicular to a transverse plane containing each of the external members 24. Translation of the crossbar 30 within the slots 23S may translate the first shaft 25 relative to the second shaft 23, which may move the internal member 26 longitudinally relative to the external members 24 between the distal position (which may correspond to a distal end of slot 23S) and the proximal position (which may correspond to a proximal end of slot 23S). When retracted from the distal position shown in FIG. 11A, past the pair of external members 24, to the proximal positon shown in FIG. 11B, the internal member 26 may apply traction to the target tissue as described herein. The pair of external members 24 may apply counter-traction to the target tissue on opposing lateral sides of the internal member 26 and re-shape the tissue as described herein.

The internal member 26 may be configured to be positioned about 0.5-3 cm, and preferably 1-2 cm, distal to the pair of external members 24 when in the distal position.

The internal member 26 may be configured to be positioned about 0.5-3 cm, and preferably 1-2 cm, proximal to the pair of external members 24 when in the proximal position.

FIGS. 12A-12C show the mechanism of retraction of a target tissue, for example an atrial wall, using an endoscopic pursestring suture retractor 22. FIG. 12A shows the retraction device 22 having a distal portion comprising an internal member 26 in a distal configuration below a pair of spaced-apart external members 24. The retraction device 22 may be substantially similar to any of the retraction devices described herein. The internal member 26 is shown advanced through a puncture 34 in the wall of left atrium 15 and engaged a distal, internal surface of the atrial wall. FIG. 12B shows the retractor 22 with the internal member 26 in a proximal configuration above two external members 24. The internal member 26 may be longitudinally movable relative to the pair of external members 24 along a plane extending between the pair of external members 24 as described herein. In some embodiments, translation of a crossbar 30 may move the internal member 26 longitudinally relative to the external members 24 between the distal position and the proximal position as described herein. The two external members 24 may be configured to engage a proximal, outer surface of the atrial wall when the internal member 26 is in the proximal position. Traction may be applied to the left atrial wall by the internal member 26 as it is retracted from the distal position shown in FIG. 12A, past the pair of external members 24, to the proximal positon shown in FIG. 12B. The pair of external members 24 may apply counter-traction to the target tissue on opposing lateral sides of the internal member 26 as described herein. The traction and counter-traction applied to the target tissue may re-shape the target tissue so as to be folded over the internal member 26 into a pair of generally vertical portions V, each having a laterally-facing surface 35 extending between the internal member 26 and one of the external members 24, as shown in FIG. 12C. The laterally-facing surfaces 35 of the tented atrial wall may allow for suture placement, for example pursestring suture placement, for instrument access to and incision closure in a hollow organ in confined and narrow anatomic situations as described herein.

In some embodiments, the internal member 26 may be configured to be advanced through the wall of the heart while the heart is beating. Alternatively or in combination, the internal member 26 may be configured to be advanced through the wall of the heart while a chest of the patient remains closed. In some embodiments, the internal member 26 may be configured to apply traction to the target tissue while the heart is beating. Alternatively or in combination, the internal member 26 may be configured to apply traction to the target tissue while a chest of the patient remains closed.

Figure 13:
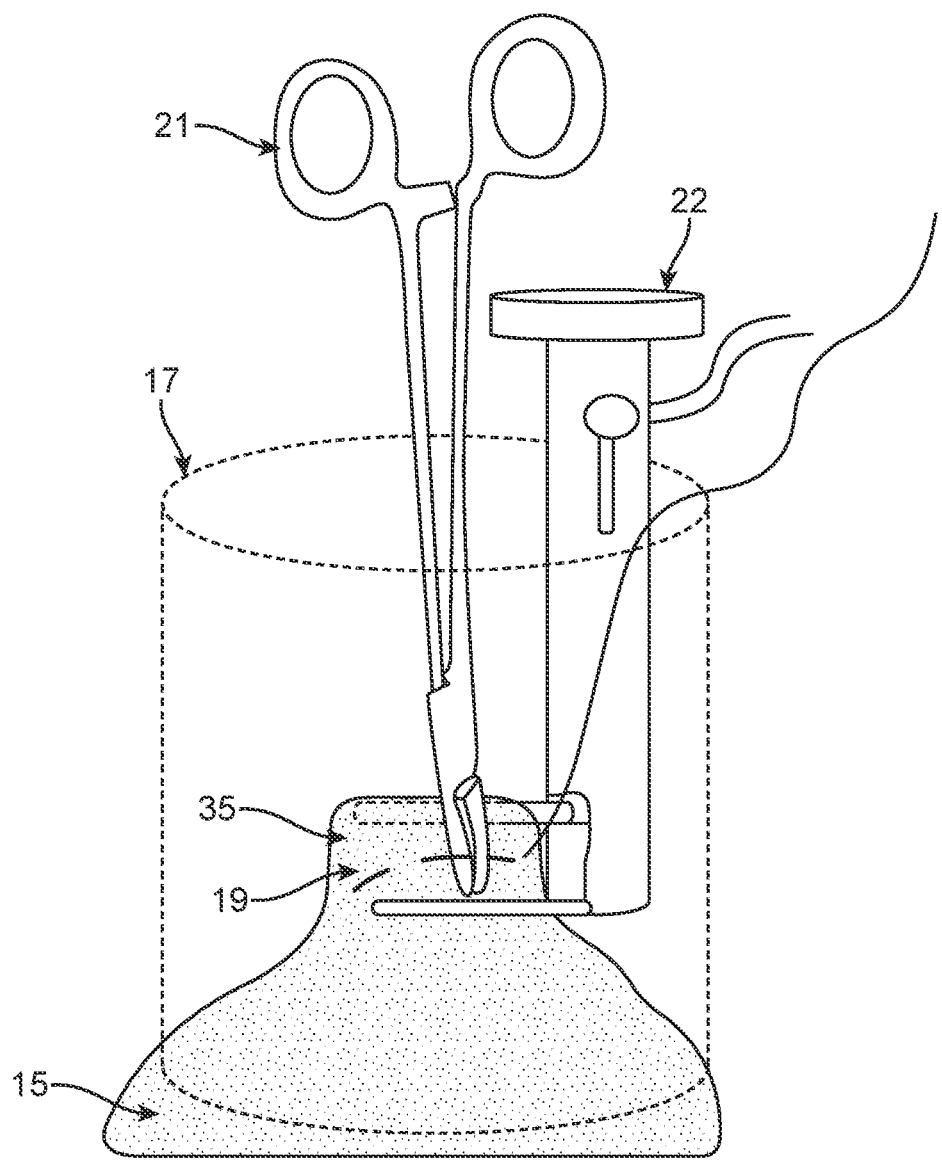
FIG. 13 shows the configuration of the curved needle and the surgical needle holder when used with an endoscopic pursestring suture retractor.

FIG. 13 shows the configuration of the curved needle 19 and the surgical needle holder 21 when used with an endoscopic pursestring suture retractor 22 to place one or more sutures in the target tissue. The one or more sutures may, for example, be placed in the tissue in a pursestring pattern as described herein. The tissue retractor 22 is shown in the proximal configuration with the internal member 26 and the external members 24 re-shaping the tissue 15 form a pair of laterally-facing walls 35 therein. Unlike the situation shown in FIG. 5 using conventional techniques, the pair of laterally-facing walls 35 may enable the surgical needle holder 21 to hold the curved needle 19 in a correct orthogonal orientation in order to place one or more sutures in the laterally-facing walls 35 of the target tissue while remaining inside the working space 17 allotted by a minimally-invasive approach, such as through a mediastinoscope or suprasternal access device as described herein. The pair of laterally-facing walls may further facilitate axial rotation of the needle holder 21 within the working space. Using the systems, devices, and methods described herein, the tissue may thus be re-shaped to facilitate the range of motion of needle holder 21 needed for suture placement within the available working space 17 of a minimally-invasive access pathway.

FIGS. 14A-14E show placement of an endoscopic pursestring suture retractor 22 into the left atrium 15 of the heart.

FIGS. 14A-14C show placement of a guidewire 37 into the left atrium 15 of the heart via a needle 36. A long needle 36 may be advanced from a remote opening in the skin of the patient, for example at the suprasternal notch as described herein, and through a working space to reach a target tissue, shown here as the roof of the left atrium 15. In some embodiments, the needle 36 may be inserted into the body of the patient via a working channel of a surgical instrument, an endoscope, a mediastinoscope, or a suprasternal access device placed through the remote opening in the body of the patient. The needle 36 may be inserted into the dome of the left atrium 15 to enable access to the interior of the heart for a guidewire 37 advanced therethrough. Correct positioning of the needle 36 in the heart of the patient may be confirmed by the presence of bright red, oxygenated blood exiting a proximal hub of the needle 36. Incorrect positioning of the needle 36 in the pulmonary artery may be confirmed by the presence dark, un-oxygenated blood. Fluoroscopy or transesophageal echocardiogram can also or alternatively be used to confirm correct positioning of the needle 36. Once the position of the needle 36 has been confirmed, the guidewire 37 may be advanced into the left atrium 15 through the needle 36 as shown in FIG. 14B. The needle 36 may then be removed from the left atrium 15 (and the patient). The guidewire 37 may be left in the atrium 37 after removal of needle 36 from the patient as shown in FIG. 14C.

FIG. 14D shows an endoscopic pursestring suture retractor 22 loaded onto the guidewire 17 following needle 26 removal. The tissue retractor 22 may be inserted into the body of the patient through an incision in the skin of the patient, for example at the suprasternal notch, as described herein. In some embodiments, the tissue retraction device 22 may be inserted into the body of the patient via a working channel of a surgical instrument, an endoscope, a mediastinoscope, or a suprasternal access device placed through the remote opening in the body of the patient. The tissue retractor 22 may be advanced along the guidewire 37 towards the puncture site 34 in the left atrium 15 as described herein.

FIG. 14E shows advancement of the endoscopic purse-string suture retractor 22 along the guidewire 37 into the left atrium 15 of the heart through a puncture site 34. The internal member 26 may be configured to be advanced through the target tissue of the left atrium 15 over the guidewire 37 slidably disposed therein as described herein. In some embodiments, the internal member 26 may be configured to create and/or expand a penetration at the puncture site 34 through which the internal member 26 may be advanced into the interior of the heart. For example, the internal member 26 may deliver electrocautery energy to the target tissue to create the penetration at puncture site 34. Alternatively or in combination, a distal end of the internal member 26 may be shaped to facilitate penetration of the tissue as described herein. The left atrium 15 may be sealed with the internal member 26 while it engages the distal surface of the left atrial wall to inhibit leakage of blood from the puncture site 34 as described herein.

After the internal member 26 has been advanced through the left atrial wall tissue, the tissue may be re-shaped as described herein to facilitate placement of one or more sutures. The suture(s) may, for example, be placed by a curved needle in a pursetring suture pattern as described herein. Alternatively or in combination, the suture(s) may be placed by a curved needle as a plurality of interrupted stitches as described herein.

After the sutures have been placed in the tissue, an incision may be made in the tissue within the one or more sutures placed therein. The incision may be made by applying electrocautery energy to the tissue with the internal member 26 as described herein. Alternatively or in combination, the incision may be made by cutting the tissue with a blade, for example a scalpel, an elongated curved blade extending from a mediastinoscope or other surgical instrument, or the like. Direct scalpel incision may be advantageous in at least some instances where the use of electrocautery may create unwanted tissue char. Alternatively or in combination, the incision may be made by advancing a cardiovascular sheath and dilator through the target tissue and dilating the dilator therein. After removal of the guidewire 37, internal member 26, and/or any other surgical instrument described herein from the tissue, the incision may be closed by tightening or knotting the one or more sutures around the incision as described herein.

After the sutures have been placed in the tissue, the internal member 26 may be removed from the target tissue and the interior of the hollow organ (e.g. heart). For example, the internal member 26 may be slidably removed over the guidewire 37 such that the guidewire 37 remains disposed through the tissue after the internal member 26 is removed. Alternatively, the guidewire 37 may be removed prior to or simultaneously with removal of the internal member 26. In some embodiments, the guidewire 37 may be removed before placement of the sutures, reintroduced after placement of the sutures, and then left in the tissue after removal of the internal member 26 to provide a pathway for additional instruments or catheters to access the heart, for example a surgical instrument to perform a surgical procedure within the heart as described herein.

In some embodiments, the heart may remain beating during one or more of the steps of inserting the endoscopic retraction device 22 into the patient, advancing the distal portion of the device 22 toward the left atrium 15, advancing the internal member 26 through the roof of the left atrium 15, applying traction to the left atrial wall, placing the one or more sutures, and/or incising the left atrial wall as described herein. It will be understood by one of ordinary skill in the art that any combination of method steps described herein may be performed while the heart is beating.

In some embodiments, the chest of the patient may remain closed during one or more of the steps of inserting the endoscopic retraction device 22 into the patient, advancing the distal portion of the device 22 toward the left atrium 15, advancing the internal member 26 through the roof of the left atrium 15, applying traction to the left atrial wall, placing the one or more sutures, and/or incising the left atrial wall as described herein. It will be understood by one of ordinary skill in the art that any combination of method steps described herein may be performed while the chest of the patient is closed.

Figure 15:
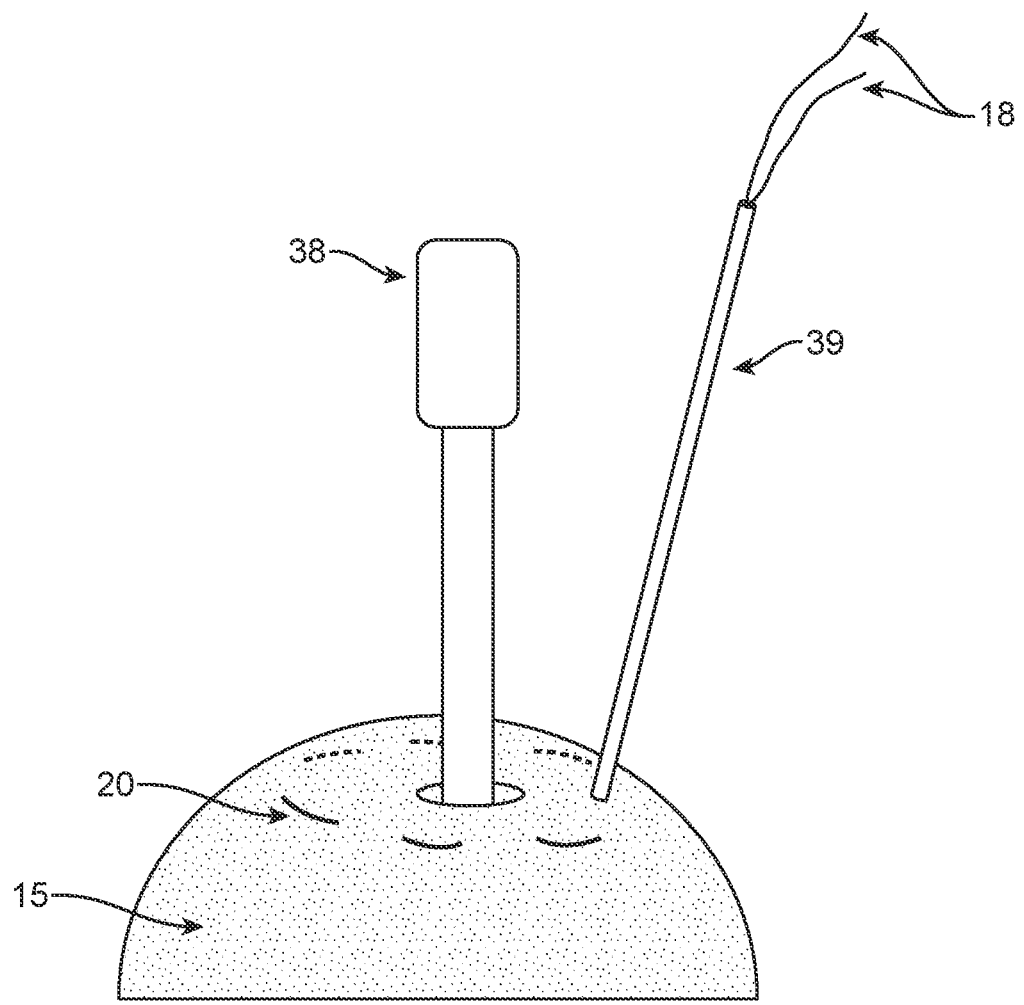
FIG. 15 shows a surgical instrument inserted through an incision in the center of a pursestring suture placed with the help of an endoscopic retractor.

FIG. 15 shows a surgical instrument 38 inserted through an incision in the center of a pursestring suture 20 placed with the help of an endoscopic retractor as described herein. After the pursestring suture 20 has been placed and the endoscopic retraction device has been removed from the tissue, at least a distal portion of the surgical instrument 38 may be inserted through the incision to access the internal structures of the hollow organ, for example the heart. The incision may be sealed around the surgical instrument 38 in order inhibit leakage of blood from the heart. For example, the sutures may be tightened around the surgical instrument 38 to seal the incision therearound. The suture ends 18 of the pursestring suture 20 may be threaded through a flexible polymer tube 39 or the like and held with a surgical clamp therein in order to keep the sutures tight around the surgical instrument 38 to maintain hemostasis. The ends of suture(s) 18 may be externalized or brought out of the body via the skin incision. Use of a clamped polymer tube 39 to maintain tension on a cinched pursestring suture 20 is referred to as a Rumel tourniquet.

The surgical instrument 38 may be configured to perform a surgical procedure inside the heart after being inserted through the incision 40. The surgical procedure may, for example, comprise at least one of mitral valve replacement, mitral valve repair, mitral annuloplasty, chordal repair, chordal replacement, leaflet resection, or leaflet coaptation. The surgical procedure may, for example, comprise at least one of atrial appendage closure, atrial ablation, pulmonary vein ablation, septal defect closure, aortic valve repair, aortic valve replacement, tricuspid valve repair, tricuspid valve replacement, implantable cardiac defibrillator (ICD) implantation, pacemaker implantation, or placement of leads for ICD's or pacemakers, myocardial biopsy, or septectomy. It will be understood by one of ordinary skill in the art that the surgical procedure will depend on the hollow organ of interest.

Figure 16:
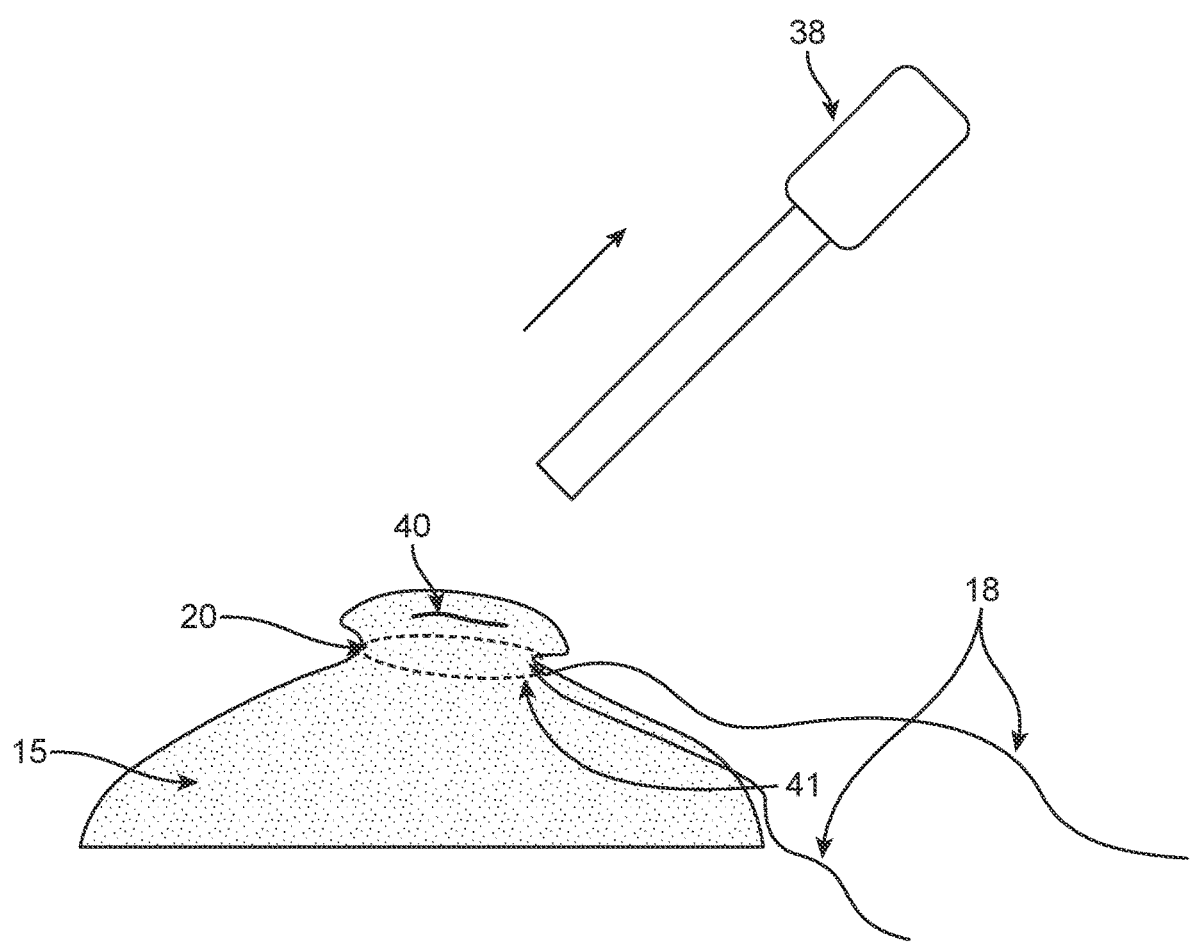
FIG. 16 shows cinching of pursestring suture to close the left atrial incision following removal of a surgical instrument from the heart.

FIG. 16 shows cinching of the pursestring suture to close the left atrial incision 40 following removal of a surgical instrument 38 from the heart. The polymer tube tensioning the suture ends 18 may be removed prior to, at the same time as, or after the surgical instrument 38 is removed from the incision 40. The incision 40 may then be closed by tightening or knotting the one or more sutures around the incision 40. For example, a pursestring suture 20 may be cinched around the incision 40 by drawing the ends 18 of the pursestring suture 20 tight. The incision 40 may then be permanently closed by forming a plurality of square knots 41 in the suture 18. Alternatively or in combination, the suture may comprise a plurality of interrupted stitches as described herein which may be knotted to close the incision 40 as described herein after the surgical instrument 38 has been removed.

Figure 17:
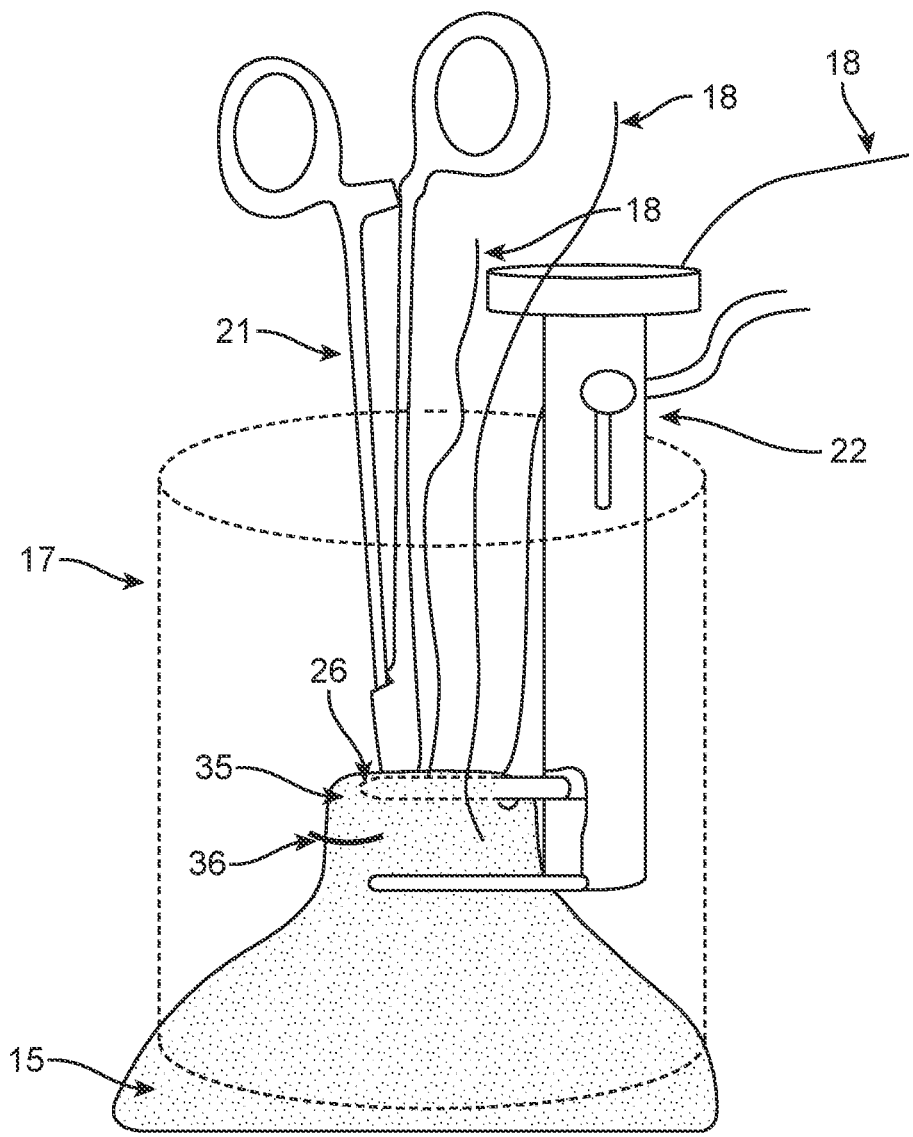
FIG. 17 shows placement of interrupted sutures in the left atrium using an endoscopic pursestring suture retractor.

FIG. 17 shows placement of interrupted sutures in the left atrium 15 using an endoscopic pursestring suture retractor 22. The tissue retractor 22 is shown in the proximal configuration with the internal member 26 and the external members 24 re-shaping the tissue 15 form a pair of laterally-facing walls 35 therein as described herein. The surgical needle holder 21 may be used to place a plurality of interrupted sutures 18 in the left atrium 15, with all devices remaining within the working space 17 of a mediastinoscopic or suprasternal approach pathway. Multiple suture strands 18 coupled to multiple curved needles may be inserted within the pair of laterally facing walls 35, distal to the position of the internal member 26, while the internal member 26 re-shapes the tissue as described herein. Following placement of the interrupted sutures 18, an incision may be created within the sutures 18 as described herein.

Figure 18A:
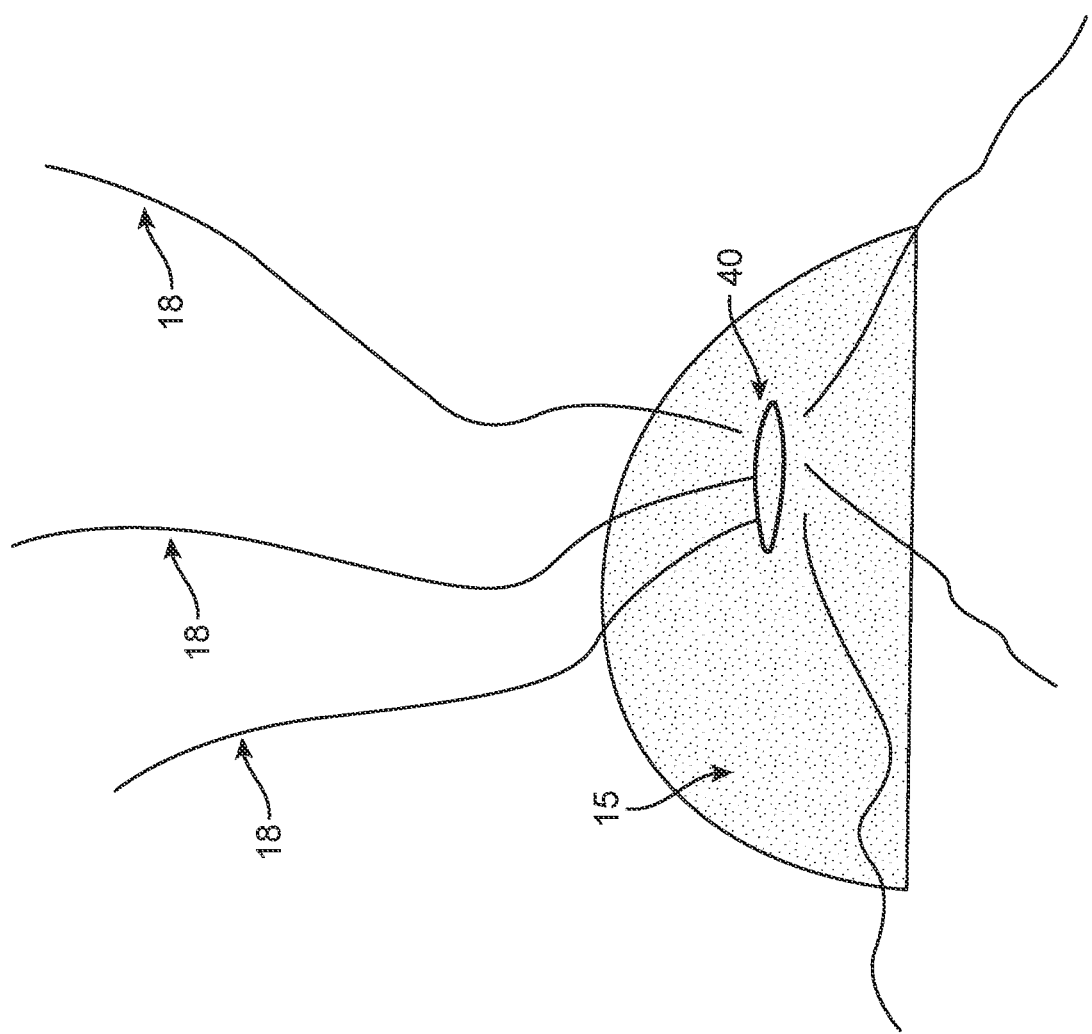
FIG. 18A shows placement of interrupted sutures around an incision in the left atrium.

FIG. 18A shows placement of interrupted sutures 18 around an incision 40 in the left atrium 15. A plurality of suture strands 18 may be spaced along the tissue wall around the atrial incision 40. The incision 40 may be closed by tying or knotting the plurality of interrupted sutures 18, or example with a plurality of square knots 41.

Figure 18B:
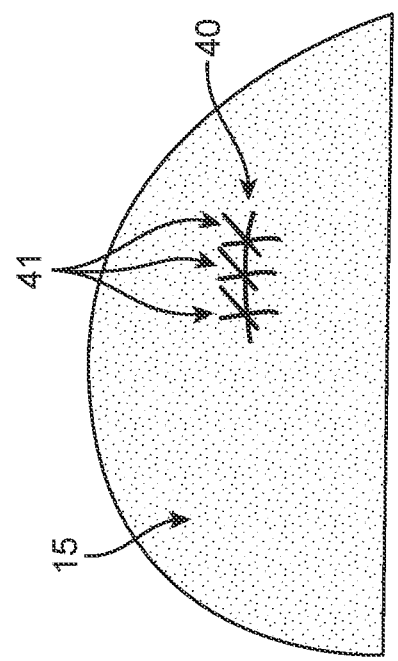
FIG. 18B shows the configuration of interrupted sutures used to close a left atrial incision.

In some embodiments, one or more of the steps for placement of the tissue retractor 22 into the target tissue shown in FIGS. 14A-14E and described herein, and/or one or more the steps for tissue retraction shown in FIGS. 12A-12B, and/or one or more of the steps for suture placement shown in FIGS. 13 and 17, and/or one or more of the steps for incising the target tissue shown in FIGS. 14A-15, and/or one or more of the steps for placement or removal of a surgical instrument shown in FIGS. 15 and 16, and/or one or more of the steps for closing the incision in the target tissue shown in FIGS. 16 and 18, and/or one or more of any of the method steps described herein may be performed while visualizing the target tissue and/or the structures along the access path to the target tissue with a visualization device. The visualization device may, for example, comprise a mediastinoscope, a camera coupled to the distal portion of the endoscopic tissue retraction device, an optical channel in the endoscopic tissue retraction device, and/or an endoscope or the like which will be known to one of ordinary skill in the art. For example, the visualization device may comprise a mediastinoscope containing an endoscope for visualization of internal structures on a video monitor.

It will be understood by one of ordinary skill in the art that the endoscopic tissue retractor devices, systems, and methods described herein may be used to place any suture pattern desired by one of ordinary skill in the art for access inside a hollow organ. For example, the endoscopic tissue retractor devices, systems, and methods described herein may be used to place a pursestring suture and/or a plurality of interrupted sutures as described herein.

It will also be understood that, although the terms first, second, etc. are, in some instances, used herein to describe various elements, these elements should not be limited by these terms. These terms are only used to distinguish one element from another. For example, a first shaft could be termed a second shaft, and, similarly, a second shaft could be termed a first shaft, without departing from the scope of the various described implementations. The first shaft and the second shaft are both shafts, but they are not the same shaft unless explicitly stated as such.

The terminology used in the description of the various described implementations herein is for the purpose of describing particular implementations only and is not intended to be limiting. As used in the description of the various described implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof The foregoing description, for purpose of explanation, has been described with reference to specific implementations. However, the illustrative discussions above are not intended to be exhaustive or to limit the scope of the claims to the precise forms disclosed. Many modifications and variations are possible in view of the above teachings. The implementations were chosen in order to best explain the principles underlying the claims and their practical applications, to thereby enable others skilled in the art to best use the implementations with various modifications as are suited to the particular uses contemplated.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of placing a suture in a tissue of a patient, comprising:
   inserting an endoscopic tissue retraction device into a body of a patient;
   advancing a distal portion of the endoscopic tissue retraction device toward a target tissue of the patient, the distal portion comprising an internal member and a pair of spaced-apart external members, the internal member being longitudinally movable relative to the pair of external members along a plane extending between the pair of external members;

advancing the internal member of the tissue retraction device through the target tissue to engage a distal surface of the target tissue;

applying traction to the target tissue with the internal member by retracting the internal member from a distal position towards and past the pair of external members to a proximal position while engaging a proximal surface of the target tissue with the pair of external members, wherein the pair of external members are configured to apply counter-traction on opposing lateral sides of the internal member, wherein the target tissue is re-shaped so as to have a pair of laterally facing surfaces each extending between the internal member and one of the external members; and placing one or more sutures in at least one of the laterally facing surfaces of the target tissue while the internal member and the pair of external members apply traction thereto.

2. The method of claim 1, further comprising making an incision in the target tissue within the one or more sutures.

3. The method of claim 1, wherein the target tissue is a wall of a heart of the patient.

4. The method of claim 3, wherein the heart remains beating during the steps of inserting the endoscopic tissue retraction device, advancing the distal portion, advancing the internal member, applying traction, and placing the one or more sutures.

5. The method of claim 1, wherein placing the one or more sutures comprises placing a pursestring suture.

6. The method of claim 2, wherein making the incision comprises advancing a cardiovascular sheath and dilator through the target tissue and dilating the target tissue with the dilator.

7. The method of claim 2, further comprising closing the incision by tightening or knotting the one or more sutures around the incision.

8. The method of claim 2, further comprising inserting a distal portion of a surgical instrument through the incision.

9. The method of claim 8, further comprising sealing the incision around the surgical instrument to inhibit leakage of blood or bodily fluids.

10. The method of claim 8, further comprising performing a surgical procedure with the surgical instrument after the surgical instrument is inserted through the incision.

11. The method of claim 10, wherein the target tissue comprises a wall of a heart of the patient and wherein the surgical procedure comprises at least one of mitral valve replacement, mitral valve repair, mitral annuloplasty, chordal repair, chordal replacement, leaflet resection, or leaflet coaptation.

12. The method of claim 10, wherein the target tissue comprises a wall of a heart of the patient and wherein the surgical procedure comprises at least one of atrial appendage closure, atrial ablation, pulmonary vein ablation, septal defect closure, aortic valve repair, aortic valve replacement, tricuspid valve repair, tricuspid valve replacement, implantable cardiac defibrillator (ICD) implantation, pacemaker implantation, or placement of leads for ICD's or pacemakers, myocardial biopsy, or septectomy.

13. The method of claim 1, wherein inserting the endoscopic tissue retraction device into the body of the patient comprises inserting the endoscopic tissue retraction device in a working channel of a surgical instrument, an endoscope, a mediastinoscope, or a suprasternal access device placed through an opening in the body of the body of the patient.

14. The method of claim 1, wherein the internal member comprises a lumen and an elastomeric seal disposed therein, the elastomeric seal being configured to inhibit flow through the lumen.

15. The method of claim 1, further comprising inserting a guidewire through the target tissue before advancing the internal member therethrough.

16. The method of claim 15, wherein advancing the internal member through the target tissue comprises slidably advancing the internal member over the guidewire, the guidewire being disposed in a lumen of the internal member.

17. The method of claim 1, wherein the endoscopic tissue retraction device comprises an first shaft coupled to the internal member and a second shaft slidably coupled to the first shaft, the second shaft being coupled to the two or more external members, and wherein retracting the internal member from the distal position to the proximal position comprises translating the first shaft relative to the second shaft.

18. The method of claim 1, further comprising visualizing the target tissue while inserting the endoscopic tissue retraction device, advancing the distal portion, advancing the internal member, applying traction, placing the one or more sutures, or making the incision.

19. The method of claim 18, wherein visualizing comprises viewing the target tissue with a mediastinoscope, a camera coupled to the distal portion of the endoscopic tissue retraction device, an optical channel in the endoscopic tissue retraction device, or an endoscope.

20. The method of claim 1, wherein the target tissue comprises a roof of the left atrium.

21. The method of claim 20, wherein the distal portion of the endoscopic tissue retraction device is advanced to the roof of the left atrium from a penetration at a suprasternal access site while the sternum and ribs of the patient remain intact.

22. The method of claim 20, wherein the internal member is advanced through the target tissue without penetrating or cutting a pericardium of the heart.

* * * * *